United States Patent [19]

Beecham

[11] Patent Number: 5,876,926
[45] Date of Patent: Mar. 2, 1999

[54] METHOD, APPARATUS AND SYSTEM FOR VERIFICATION OF HUMAN MEDICAL DATA

[76] Inventor: James E. Beecham, 8820 Cortile Dr., Las Vegas, Nev. 89134

[21] Appl. No.: 910,062

[22] Filed: Aug. 6, 1997

Related U.S. Application Data

[63] Continuation-in-part of Ser. No. 686,211, Jul. 23, 1996.
[51] Int. Cl.[6] ...................................................... C12Q 1/70
[52] U.S. Cl. .................................... 435/5; 435/4; 422/56; 422/57; 422/58; 422/63; 422/67; 364/400; 364/409; 364/413; 364/413.01; 382/2; 382/4; 382/115; 382/124; 382/125; 382/126
[58] Field of Search .............................. 435/4, 5; 422/56, 422/57, 58, 63, 67; 364/400, 409, 413, 413.01; 382/2, 4, 115, 124, 125, 126

*Primary Examiner*—Jeffrey Stucker
*Attorney, Agent, or Firm*—Seed & Berry LLP

[57] ABSTRACT

A method and apparatus for collecting medical data from a test subject while optionally preserving anonymity for the test subject. The method includes steps of collecting a sample from the test subject and taking biometric data from the test subject. The biometric data permit a high order of probability of correlation of the test subject with the sample and with test results derived from the sample. The method optionally further includes a step of providing the test subject with a unique correlating code also for permitting unique correlation of the test subject with the sample and with test results derived from the sample, and further desirably includes a step of labeling the sample with information including the biometric data.

17 Claims, 10 Drawing Sheets

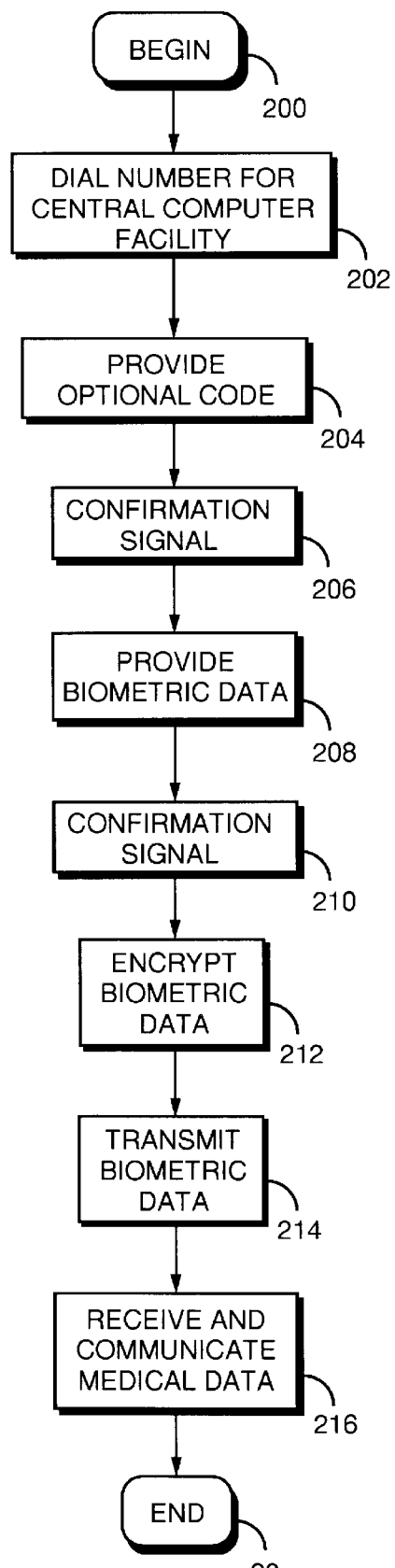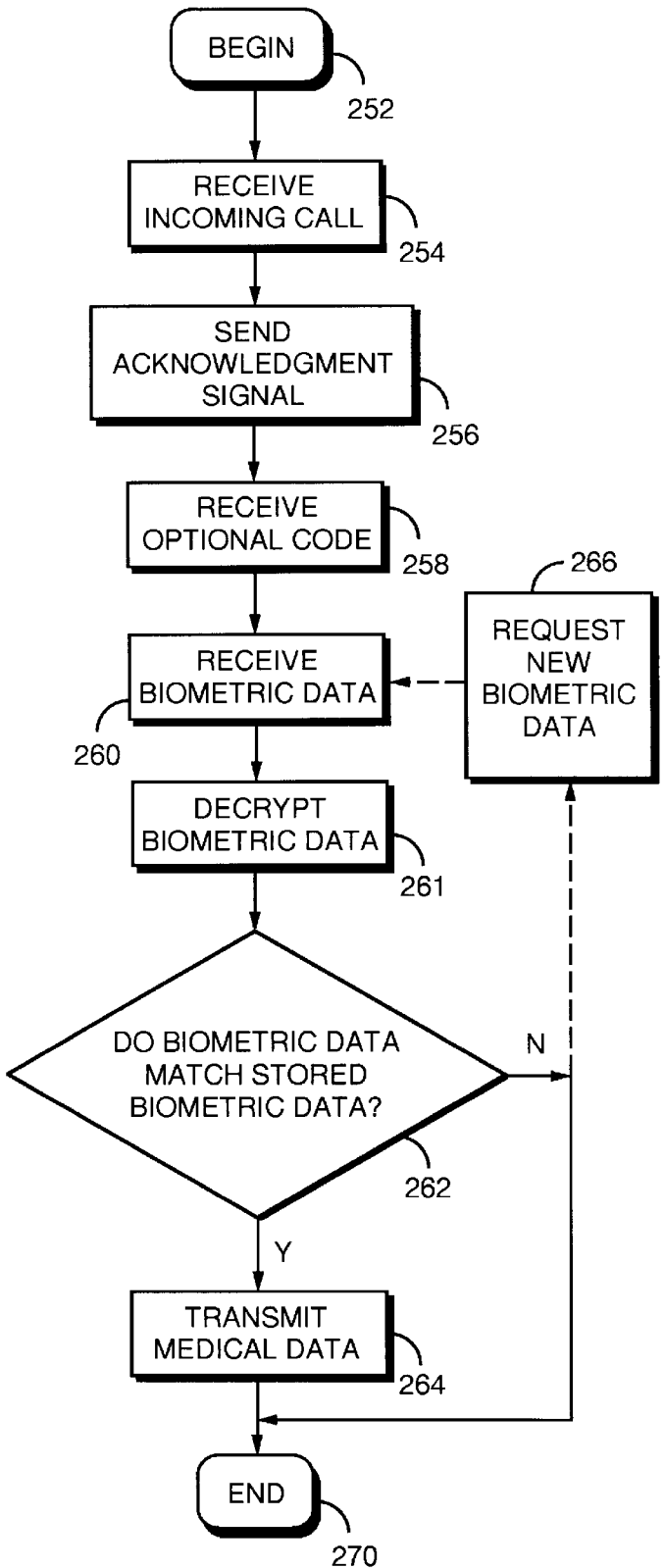
FIG. 8
FIG. 9

METHOD, APPARATUS AND SYSTEM FOR VERIFICATION OF HUMAN MEDICAL DATA

RELATED APPLICATIONS

This application is a continuation-in-part of U.S. patent application Ser. No. 08/686,211, filed on Jul. 23, 1996, which is owned by the same entity as the instant application.

BACKGROUND OF THE INVENTION

1. Field of the Invention

This invention relates to a method, apparatus and system for anonymously providing medical data for humans including infectious status.

More particularly, the present invention relates to anonymously providing medical data for humans via unforgeable correlation characteristics.

In a further and more specific aspect, the instant invention concerns a method and apparatus for voluntarily and anonymously providing medical data for humans and allowing the subject to share that information with a chosen associate or associates.

2. Prior Art

Medical data collection, storage and display systems of great variety in construction and purpose are often employed for medical and non-medical purposes. Examples include the systems described in U.S. Pat. No. 4,737,912 entitled "Medical Image Filing Apparatus", issued to Ichikawa, hereby incorporated herein by reference, directed to a medical image filing and display system and the like.

Another example is described in U.S. Pat. No. 5,193,541 entitled "Health Examination Method And System Using Plural Self-Test Stations And A Magnetic Card", issued to Hatsuwi, hereby incorporated herein by reference. This patent is directed to a system for storing medical data on magnetic media contained on a card, wherein the patient provides samples and the like to a variety of testing stations that also record the self-test data on the card.

A further example is taught in U.S. Pat. No. 5,325,294 entitled "Medical Privacy System", issued to Keene, hereby incorporated herein by reference. This patent describes a system and method for retrieving medical data from a database and sharing these medical data voluntarily with another party while protecting against unauthorized access by unauthorized parties.

A feature common to such systems is a means for identifying a particular patient or client and the associated, relevant medical records. Two particular and possibly overlapping areas where such concerns arise are: (I) sample collection and (II) testing to determine human health characteristics including infectious status of humans, and especially HIV status.

§ I. Sample collection.

Various types of samples may be collected for various purposes, including blood typing, drug testing and testing for infectious or genetic diseases. Depending on the purpose of the testing, various specific biological specimens may be collected. Often, but not always, these are bodily fluids. In some cases, tissues, hair or nail clippings may be preferred.

A. Urine testing.

Several commercially available urine test specimen collection devices and systems are known for collecting and identifying human urine donated as test material. Typically, these collection systems have a plastic receptacle or reservoir into which the test subject urinates and a plastic top or cover which attaches by threaded attachment.

As with most specimens for laboratory testing, it is desirable to have a way of linking the specimen as originating from the test subject from which the specimen is collected. This linked identification is needed in order to allow the testing laboratory to report results correctly linked to the individual from whom the test material was obtained. Typically, the name of the test subject and other identifying indicia are written by hand on a label (or, alternatively, a computer-generated label is prepared including the linking data) and the label is affixed by adhesive sticker to the urine container or urine collection device side wall.

This label, attached either after or preferably prior to urine donation, is affixed to the receptacle side wall rather than the top because the currently available urine containers have tops which are often interchangeable from container to container. Thus, a label attached only to the top can be inadvertently transferred with another top and transferred to another container, incorrectly placing thereby the name of one patient onto the urine container holding the urine of a different patient. This may result in erroneously reported lab results leading to improper diagnosis and treatment of the patient or improper identification of one individual as having used some drug or substance.

Further, in testing of human urine in the laboratory, there is a need from time to time for anonymity in certain circumstances such as in double blind studies or where the test subject wishes to have anonymity as in HIV testing and in certain circumstances for urine drug testing associated with employment. In such circumstances, one known method for accomplishing the task of secure and specific identification of the specimen to the test subject while maintaining anonymity has been to attach a unique alphanumeric identifying number or code via a label that is attached to the sample collection container or device.

A first limitation of such a numerical system is that one subject may give the corresponding chit to a second individual and then the second individual may portray the test material and test results as originating from and linked to him- or her-self rather than from the true test subject. A further limitation is that the alphanumeric code, if provided to the test subject or researcher in the form of a disposable paper chit, may be lost. Correlation of the test specimen and container or device may then be hindered or completely corrupted. Additionally, computerized linkage of an alphanumeric code to other data may be subject to input error by a keyboard operator in some circumstances.

Where these types of records are drug testing results, they are usually collected by and for a single employer; a subsequent employer may well be denied access to these records for any of many reasons. A prior employer may wish to limit liability against suit by a dismissed employee, and the employee may well dispute the accuracy of the testing process. Because samples are typically labeled before or, alternatively, after testing, possibility of confusion between test subjects is a very real concern.

What is needed is a system, apparatus or method wherein a secure and verifiable yet anonymous identification and linkage is established between the urine sample collection device or container and the urine donation. Ideally, this linkage occurs or is established simultaneously with collection of the urine sample. Furthermore, there is a need for urine specimen collection devices that are anatomically easy to hold and use and that, at the same time, allow for ease of affixing of identifying data to the collection device.

B. Phlebotomy blood sample collection.

Samples of blood are typically collected by puncturing the skin and removing by vacuum a sample of whole blood. A tourniquet is typically applied to the arm or in some cases the leg of the test subject and the skin surface is swabbed with alcohol to disinfect. Subsequently the test subject is asked often to grip a rubber grip so that the natural muscle compression leading to blood flow in the venous system is utilized to cause the vein to engorge and swell indicating that blood volume has increased in the vein. Then a needle attached to a syringe is inserted into the vein and a quantity of blood is removed. Other common means of phlebotomy or blood sample procurement are via indwelling lines such as catheters or by blood lancet puncture of skin such as infant heel and subsequent daubing of blood from skin surface into capillary tubes or absorbent paper card.

C. Oral mucosal transudate sample collection.

Oral mucosal transudate (OMT) samples may be collected and these may be tested to determine either infectious disease status or to identify foreign substances, such as therapeutic or recreational drugs, present in the body. Breathalyzer tests are frequently administered, especially in the context of testing drivers for alcohol intoxication. In both instances, chain of custody issues may render the sample inoperative or inappropriate in medical evaluation and/or as legally operative evidence.

D. Breathalyzer sampling.

Commercially available breath test collection devices are employed, for example, to assess human alcohol level by measurement of breath alcohol levels. Typically these devices utilize roadside measurement and the test is administered by law enforcement officials. Use of the resulting alcohol measurement number is envisaged for subsequent legal proceedings. In order to do so, a positive means for identifying the test subject is needed. All of the currently available breathalyzer systems incorporate means of identification of the specimen as originating from the test subject from whom the specimen is collected such as photo or driver's license number or the like. In order to maintain specimen integrity and to link the results to the individual from whom the breath test material was taken, the name or other numerical identifier of the test subject is typically written or affixed by coded sticker or the like attached to the printout of the test results. The limitation of such a numerical identification system is that one attorney may allege that the corresponding test subject is not the attorney's client but rather some other individual and then the test results may not be admissible in court. Alternatively, the test subject is taken to a hospital where a blood sample is taken and a legal chain of custody is maintained for results to be acceptable to a court of law. This procedure involves time and expense for the law enforcement official and laboratory.

E. Hair and fingernail sample collection.

Hair and fingernails both include metabolites of substances ingested by the subject and either may be used to determine drug use in particular. Both types of samples are subject to contamination from external sources, e.g., walking through a room laden with marijuana smoke or working with the hands immersed in chemical baths. For these and other reasons, testing of this type of specimen has not met with widespread acceptance. Additionally, chain of custody is an issue relevant to testing these types of specimens.

§ II. Sample evaluation.

Once collected, biological samples are evaluated to determine a variety of characteristics. These include (A) drug testing, (B) testing for diseases such as infectious diseases and (C) testing to identify genetic predisposition for developing disease.

A. Drug testing.

Drug testing may be carried out on any of many types of samples collected from a test subject. Urine testing is particularly common and is widely believed to be less intrusive than testing that measures for metabolites over a longer interval of the test subject's recent life. Hair samples, for example, may be tested to determine drug usage over a relatively long period of time, however, relatively little is known about the actual accuracy of such tests. Breath samples and oral mucosal transudate samples may provide useful or legally significant information regarding recent drug use or about disease status of the individual.

B. Infectious disease monitoring.

Human disease status is highly confidential information subject to misuse by any of a variety of agencies or individuals. For example, some doctors will advise patients not to seek human immunodeficiency virus (HIV) testing via the doctor because the records generated in the process of testing for HIV may be used by insurance companies to deny insurance coverage to the individual requesting the test results.

The reasoning seems to be that if the individual sought to ascertain HIV status information, the individual must have reason to suspect a positive HIV status. The individual therefore is adjudged likely (i) to have engaged in high-risk behavior, (ii) to continue to engage in high-risk behavior and (iii) to have an enhanced probability (compared to other population segments) of developing (a) HIV-positive status and (b) later, acquired immune deficiency syndrome (AIDS), presently a frequently fatal condition. People may well be denied employment if it is suspected that they are at risk of developing an HIV-positive status or of contracting AIDS subsequent to infection by HIV.

Accordingly, it is desirable, particularly with respect to HIV testing, to be tested in a way that completely protects the individual identity of the test subject. One such system is provided in some states through Planned Parenthood, which (i) collects a blood sample from the test subject and (ii) collects whatever identifying indicia the test subject cares to provide, such as a pseudonym. The agency typically then (iii) links the identifying indicia, the test sample and a unique identifying code or serial number in a computer database or other log and (iv) informs the test subject that test results are to be expected to be available following a set interval of one to two weeks, which interval is for shipping the test sample to a suitable laboratory or other testing facility and receiving the results of the analysis therefrom.

The test sample and code or serial number are then (v) sent to a remote site for testing and analysis. Results are then (vi) sent back to the test site (or any other designated place). The test subject (vii) returns to the test site or goes to a designated office and (viii) is advised of the test results. If warranted, (ix) appropriate counseling is provided along with follow-up services. Additionally, (x) a paper record is often provided with an indication of the test results.

Unfortunately, because the test subject often provides a pseudonym, a third party has no way of knowing that a particular record is actually the product of a test conducted on samples provided by the individual presenting such a record. Moreover, the paper record is easily forged or mutilated to alter the information contained thereon, in part because there is no standard or unforgeable format for such records. In short, this system affords an individual test subject great confidence in both the anonymity and the trustworthiness of the test result, but this system does not provide the test subject with any verifiable way of providing the test results to a third party. Additionally, recent multiple-drug therapies can reduce presence of HIV and indicia of HIV to immeasurably low levels but these therapies introduce detectable levels of drugs into the bloodstream of the test subject.

Further, the situations in which people might meet and desire to know or communicate to each other the infectious disease status of one another do not lend themselves to accessing of data during the course of normal business hours. Social settings in which persons might meet and form a mutual desire for sexual activity tend to be focused on hours other than normal business hours, for example, in the evening at a nightclub. If there were a method for reliably and anonymously exchanging information such as indicia of HIV-negative status and the date on which the sample providing this result was collected, it would need to be useful in such settings or in conjunction therewith in order to be effective in controlling the spread of this deadly disease.

Accordingly, it is desirable to provide reliable data on health and/or infectious status in an anonymous fashion whereby the person viewing the data has some assurance that the data correspond to the individual with whom they are considering carrying out such activities. However, this alone is not necessarily sufficient because it is desirable to be able to have access to the data on a twenty-four-hour-a-day basis, and also because identification cards and the like may not correspond to the bearer thereof. Therefore, it is appropriate and useful to base the correlation process on parameters unique to the individual whilst continuing to ensure anonymity of the test subject, the test results and the fact that the test subject had the testing performed.

C. Genetic testing.

Laboratory testing for genetic markers of disease and hereditary susceptibility to diseases or specific conditions is a rapidly developing area of medicine. Current methods include DNA and RNA analysis based on hybridization techniques such as fluorescence in situ hybridization, restriction length polymorphism and polymerase chain reaction for amplification of nucleic acid.

The diseases and hereditary predispositions to disease for which genetic testing is currently available include sickle cell anemia, muscular dystrophy of various types, fragile X disease, chronic myelogenous leukemia, predisposition to development of cancer such as breast cancer gene BRCA-1 or colon cancer gene. These issues have had considerable public attention focused on them because they may be used to discriminate against some people in specific settings, e.g., in the making of hiring and downsizing decisions, in permitting the individual to obtain health insurance and the like.

A woman with BRCA1 has a lifetime risk of developing breast cancer of 85% versus 11% lifetime risk for a woman who does not have the BRCA1 gene. Surveillance by mammogram or other means to detect the earliest sign of tumor in the high risk women is prudent. Newer techniques, such as DNA chip technology, portend cost reductions and more widely available testing in the near future.

In order to combat these varied problems, some form of correlation that is unique to the individual, that is not based on a photograph or the like of the individual and that does not employ a transferable or forgeable identity device (such as an identity card) is required. The form of correlation needs to be highly reliable and also must operate rapidly in real time to provide "go/no-go" identification in a short period of time (e.g., a minute or less).

While the various mentioned prior art devices function as apparatus for collecting, storing and retrieving human medical data, certain inherent deficiencies preclude adequate, satisfactory performance of the purpose of reducing risk of exposure of the individual identities of persons using the system.

It would be highly advantageous, therefore, to remedy the foregoing and other deficiencies inherent in the prior art.

Accordingly, it is an object of the present invention to provide improvements in anonymous human health and/or medical data collection and retrieval.

Another object of the present invention is the provision of an improved method and apparatus for anonymously providing human health and/or medical data in a secure and tamper-free fashion that allows a person to share those data with another party.

An additional object of the instant invention is the provision of an improved method and apparatus for providing human health and/or medical data in a way that allows another party to have great confidence that the data provided are reliable and that they correspond to the party rendering the data available to them.

Still a further additional object of the present invention is to provide an improved method, apparatus and system for anonymously collecting human health and/or medical data and allowing retrieval of the data in a secure fashion that permits twenty-four hour access thereto.

And another object of the present invention is to provide an improved method, apparatus and system for collecting, storing and retrieving human health and/or medical data in an anonymous fashion that does not rely on forgeable identification devices.

Still another object of the present invention is the provision of a method, system and apparatus for displaying and sharing human health and/or medical data with a chosen person or people.

Yet another object of the instant invention is to provide a method, system and apparatus for retrieving human health and/or medical data in a secure fashion that also provides a high degree of confidence in the test subject of the anonymity of the test subject.

Yet still another object of the instant invention is the provision of a method, system and apparatus for identifying individuals free of HIV indicia in a reliable and anonymous fashion in order to stem the spread of a presently a frequently fatal disease.

And a further object of the invention is to provide a voluntary method, system and apparatus for identifying individuals who are free of HIV indicia and/or indicia of recreational drug usage without risk of compromising the individual's identity.

Still a further object of the immediate invention is the provision of a method, apparatus and system for collecting, storing and retrieving human health and/or medical data in a secure and tamper-free fashion that also guarantees that (i) the individual retrieving the data is also the individual to whom the human health and/or medical data are pertinent and (ii) that the individual retrieving the data has access only to medical records relevant to that specific individual and no other medical data.

Yet a further object of the invention is to provide a new system and method for anonymously testing for human HIV status and/or antigens or antibodies for human diseases and/or drug levels of therapeutic drugs known to be used in treatment of infectious diseases and/or drug levels of "recreational" drugs.

And still a further object of the invention is the provision of method and apparatus, according to the foregoing, which is intended to allow rapid, real-time access to human health and/or medical data and the date of collection of the sample from which the data are derived, by only the donor of the sample from which the information is derived, while preserving the anonymity of the test subject and also providing any other party with whom the test subject chooses to share the data great confidence that the data apply to the test subject.

SUMMARY OF THE INVENTION

Briefly, to achieve the desired objects of the instant invention in accordance with a first preferred embodiment thereof, provided is a method, a system and an apparatus for collecting medical data from a voluntary test subject while optionally preserving anonymity for the test subject. The method includes steps of collecting a sample from the test subject and taking biometric data from the test subject. The biometric data permits correlation of the test subject with the sample and with test results derived from the sample. The method desirably but not essentially includes a step of providing the test subject with a unique correlating code also for permitting unique correlation of the test subject with the sample and with test results derived from the sample. The method also desirably but not essentially includes a step of labeling the sample with information including the biometric data.

The method desirably but not essentially further includes a step of labeling the sample with the unique correlating code, and further desirably but not essentially includes a step of labeling the sample with information including the biometric data.

The method desirably but not essentially further includes steps of analyzing the sample to provide a result, the result for determining infectious status of the test subject and/or presence of antigens or antibodies for human diseases and/or presence of drug levels of therapeutic drugs known to be used in treatment of infectious diseases and/or presence of drug levels of "recreational" drugs and/or genetic testing, linking the result, the biometric data and the unique correlating code together to form a single record and storing the single record in a database.

In a preferred embodiment, the method includes a step of collecting a blood sample from the test subject and the step of taking biometric data from the test subject desirably includes a step of electronically scanning finger print or hand geometry data from the test subject.

Preferably, the steps of collecting a blood sample from the test subject and the step of electronically scanning finger print or hand geometry data from the test subject occur contemporaneously (and preferably, simultaneously) in a single data collection device.

In a second preferred embodiment, the invention contemplates a method for performing medical tests on a voluntary test subject and correlating medical results from the medical tests via correlating indicia while preserving anonymity of the test subject. The method includes steps of receiving a test sample taken from the test subject and reading biometric indicia from a label on the test sample. The biometric indicia permit correlation of the test subject with the sample and with test results derived from the sample. The method also includes steps of analyzing the test sample to derive a result indicative of medical condition of the test subject, linking the biometric indicia and the result to form a single record and recording the single record in a database.

The method desirably but not essentially also includes a step of reading an alphanumeric correlation code from the label. The alphanumeric code provides a unique one-to-one correspondence to the biometric indicia and the test sample. The method optionally includes steps of linking the alphanumeric correlation code, the biometric indicia and the result to form the single record and recording the single record in a database.

The step of analyzing the test sample desirably includes a step of analyzing a blood sample for evidence of presence of human immunodeficiency virus and/or presence of antigens or antibodies for human diseases and/or presence of drug levels of therapeutic drugs known to be used in treatment of infectious diseases and/or presence of drug levels of "recreational" drugs and/or genetic testing and the step of reading biometric indicia from a label on the test sample desirably includes a step of reading biometric indicia including electronically scanned fingerprint or hand geometry information corresponding to the test subject.

In a further preferred embodiment, the invention includes an apparatus for collecting biological samples to be analyzed to provide medical data from a voluntary test subject while optionally preserving anonymity of the test subject. The apparatus includes a sample collection apparatus for collecting a biological sample from the test subject and a biometric data collection device. The biometric data collection device collects biometric data permitting positive correlation of the biological sample with the test subject. The apparatus desirably includes an apparatus for labeling the biological sample with the biometric data and the date of collection and optionally includes an apparatus for providing a unique alphanumeric code to the test subject, the unique alphanumeric code for permitting positive correlation of the biological sample with the unique alphanumeric code. The apparatus for labeling labels the biological sample container with the unique alphanumeric code.

In another preferred embodiment, the sample collection apparatus includes a blood sample collection device and the biometric data collection device includes a fingerprint or hand geometry scanning device. The sample collection apparatus and the fingerprint or hand geometry scanning device comprise a single unit adapted to collect the biometric data and the biological sample contemporaneously and preferably simultaneously.

In yet another preferred embodiment, the invention includes an apparatus for performing medical testing on a voluntary test subject and correlating medical results from the medical testing with correlation indicia whilst preserving anonymity of the voluntary test subject. The apparatus includes a label reader for reading from a label biometric indicia (e.g., stored in bar code form) and a date of sample collection on a container for holding a biological test sample from the voluntary test subject, an analyzer for analyzing the biological test sample to provide a test result including evidence of infectious status of the voluntary test subject and/or presence of antigens or antibodies for human diseases and/or presence of drug levels of therapeutic drugs known to be used in treatment of infectious diseases and/or presence of drug levels of "recreational" drugs and/or genetic testing, and a computer coupled to the label reader and to the analyzer. The computer links the biometric indicia bar code from the label reader, the date and the test result to provide a single record and for storing the single record in a database.

In still another preferred embodiment, the invention includes method for retrieving medical data from a database. The method includes steps of providing a biometric reading by a user, receiving medical data from a database when the biometric reading positively correlates with a biometric reading associated with the medical data stored in the database and displaying the medical data only in response to the user's biometric reading whose medical records are being accessed, to either the user or those whom the user has selected or with whom the user wishes to share the data.

BRIEF DESCRIPTION OF THE DRAWINGS

The foregoing and further and more specific objects and advantages of the instant invention will become readily apparent to those skilled in the art from the following detailed description of preferred embodiments thereof taken in conjunction with the drawings in which:

FIG. 8 is a flowchart describing user steps involved in a second preferred embodiment of a secure data retrieval system, in accordance with the teachings of the instant invention;

FIG. 9 is a flowchart describing system steps involved in the second preferred embodiment of a secure data retrieval system, in accordance with the teachings of the instant invention;

DETAILED DESCRIPTION OF THE PREFERRED EMBODIMENT

A first portion of the detailed description, § I, is concerned with sample collection and identification, and with storage of medical data in a database. A second portion, § II, is concerned with retrieval of the medical data from a database via a biometric key, whether the data and/or sample(s) were initially identified via biodata keys or were subsequently added to the database from a trusted source and labeled with a biometric identifier at the time that the data were added to the database. A third section, § III, discusses a series of specific examples of sample collection techniques and apparatus for linking biological samples to biometric keys specific to the individual from whom the samples were obtained.

§ I. Sample and data collection and identification.

Figure 1:
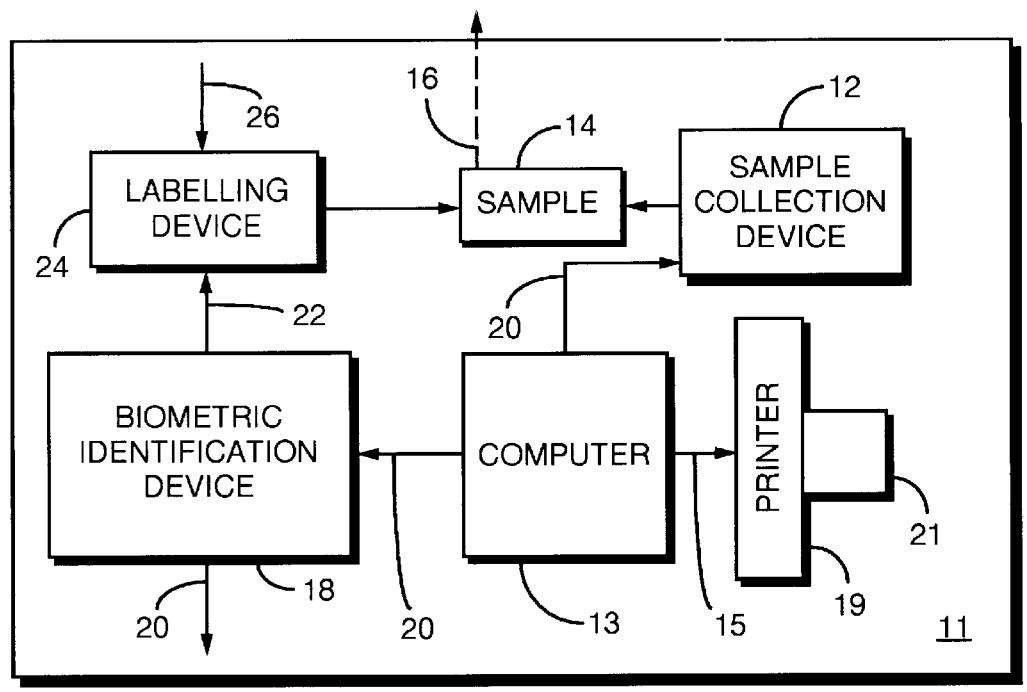
FIG. 1 is a schematic illustration of a collecting station for taking (i) a biological sample from a test subject and (ii) collecting correlating data pertinent to the test subject, in accordance with the teachings of the instant invention.
Figure 2:
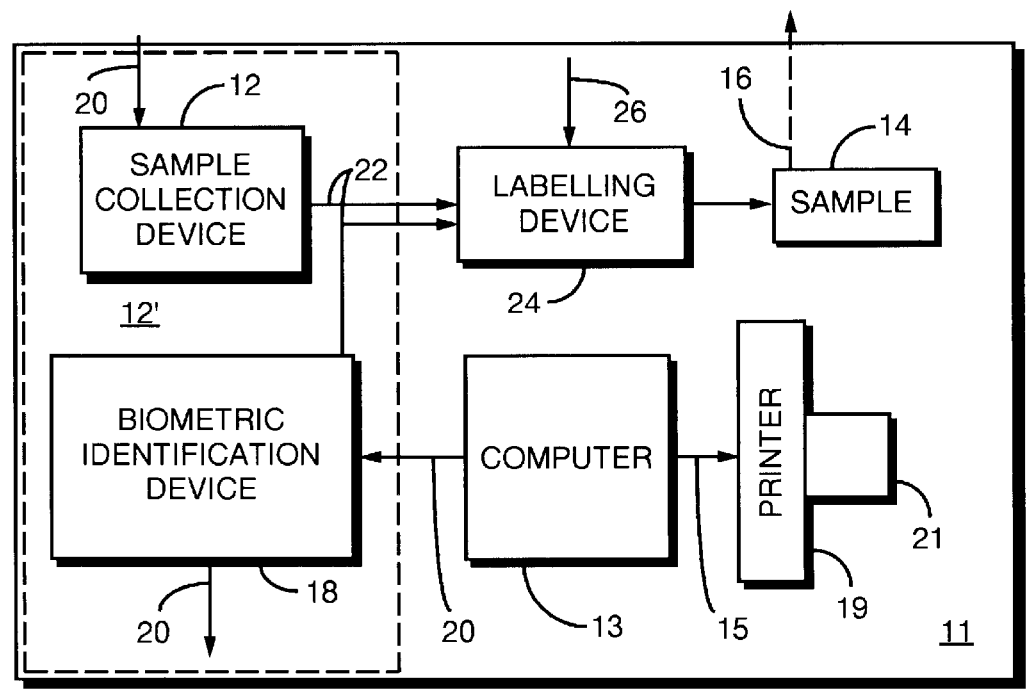
FIG. 2 is a schematic illustration of a collecting station for contemporaneously (and preferably simultaneously) taking (i) a biological sample from a test subject and (ii) collecting correlating data pertinent to the test subject, in accordance with the teachings of the instant invention.

Turning now to the drawings, in which like reference characters indicate corresponding elements throughout the several views, attention is first directed to FIGS. 1 and 2, illustrating a data collection station, generally designated by the reference character 11, for taking (i) a biological sample from a voluntary test subject and (ii) collecting correlating biometric data pertinent to the test subject, and provided with biometric scanner or correlation device 18 in accordance with the teachings of the instant invention. The arrangement of FIG. 2 provides a single apparatus 12' for contemporaneously (and preferably simultaneously) taking (i) a biological sample (e.g., blood or fingernail shavings) from a test subject and (ii) collecting correlating data pertinent to the test subject in accordance with the teachings of the instant invention. This arrangement is preferred for sample collection stations 11 operating without a human caretaker and for maintaining the integrity of the biometric data and sample collection process as is described in more detail below.

It will be appreciated that many different types of biometric scanners 18 could conceivably be employed to realize the desired function for biometric scanner 18. For example, human fingerprints provide unique indicia of identity, while automatic scanning of hand geometry may also be employed for attempting to identify specific individuals.

Techniques for automatically scanning fingerprints are described in U.S. Pat. No. 5,465,303, "Automated Fingerprint Classification/Identification System And Method", Levison et al. and U.S. Pat. No. 5,222,152, entitled "Portable Fingerprint Scanning Apparatus For Identification Verification", issued to Fishbine et al., which patents are hereby incorporated herein by reference.

While such systems are readily used and do not require removal of clothing etc. in most climates, one disadvantage of these types of systems is that certain classes of persons may already have their fingerprints on file. These classes of persons include but are not limited to law enforcement officials, persons holding governmental security clearances, persons holding certain types of permits or personal property for which fingerprints are required, members of many State Bar organizations and other people.

These persons may not feel that a system based on fingerprinting as a means of access provides a degree of anonymity sufficient to promote use of the system. Other possible methods of correlation might include toeprints, which are not usually on file, but this would require a person to remove their footgear in order to use the system and also might lend itself to the spread of annoying conditions such as athlete's foot.

Other types of biometric data successfully used for positive identification or correlation of an individual include dental records, anatomical geometries, retinal patterns, speech recognition or, for that matter, gene sequences or other chemical biodata that uniquely identify a particular individual with a high degree of confidence in the accuracy of the identification.

One preferred system that uses fingerprint indicia but that does not necessarily store fingerprint images per se is the SACMAN™ fingerprint scanning device available from Secure Access Control Technologies, Inc., located at 4620 S. Valley View, Suite A, Las Vegas Nev. This system uses a unique form of vector analysis of rastered fingerprint data taken at a resolution of, e.g., one thousand dots per inch.

Several passes through the data clean the data up and optimize the image. The data are then converted from raster form to vector line types, which are then employed to classify the print. The system maps a scanned print into a fixed coordinate system in order to preserve the same general origin for the fingerprint data. This system has advantages of: (i) a high degree of confidence in recognition of the vector line scan data, (ii) tolerance to micro feature changes and/or print contamination and (iii) security in that this system does not necessarily store fingerprint images per se. The system also lends itself to generation of index keys for large databases, allowing for very fast identification of people or data.

It will be appreciated that positive correlation of biometric data need not necessarily provide unique identification of a particular individual when a second technique for associating a specific test subject with a specific test result is employed. For example, when a unique serial number known to the test subject is coupled with biometric indicia for providing positive correlation of the test subject and sample, the degree of confidence a third party might have that the test results correspond to the individual could be quite high (even approaching certainty) if the biometric data alone would only provide, for example, a positive correlation carrying at least 95% confidence that the subject was correctly identified (as used herein, the term "positive correlation" means "a high order of probability of identification", i.e., a 95% certainty or better of identification). This means that the biometric data need not be exhaustive and that reduced datasets may be employed for the purpose of reducing the amount of biometric data that must be collected, transmitted and correlated.

Feature recognition based on face geometry is described in U.S. Pat. No. 4,975,969 entitled "Method And Apparatus For Uniquely Identifying Individuals By Particular Physical Characteristics And Security System Utilizing Same", issued to Tal, and in U.S. Pat. No. 5,012,522 entitled "Autonomous Face Recognition Machine", issued to Lambert, which patents are hereby incorporated herein by reference.

Identification techniques based on retinal patterns are described, for example, in U.S. Pat. No. 5,369,415 entitled "Direct Retinal Scan Display With Planar Imager", issued to Richard et al., and in U.S. Pat. No. 5,359,669 entitled "Remote Retinal Scan Identifier", issued to Shanley et al., which patents are hereby incorporated herein by reference. Identification based on speech recognition is described, for example, in U.S. Pat. No. 4,961,229 entitled "Speech Recognition System Utilizing IC Cards For Storing Unique Voice Patterns", issued to Takahashi, which patent is hereby incorporated herein by reference.

Identification based on gene sequences or other chemical biodata that uniquely identify a particular individual with a high degree of confidence in the accuracy of the identification is described in U.S. Pat. No. 5,270,167 entitled "Methods Of Identification Employing Antibody Profiles", and in U.S. Pat. No. 4,880,750 entitled "Individual-Specific Antibody Identification Methods", both issued to Francoeur, which patents are hereby incorporated herein by reference.

An algorithm suitable for searching a database of entries for a match for any of the above-noted biometric classification techniques is described in U.S. Pat. No. 5,479,523, entitled "Constructing Classification Weights Matrices For Pattern Recognition Systems Using Reduced Element Feature Subsets", issued to Gaborski et al.

A preferred form of biometric classification for use with the present invention is automated scanning of hand geometry. Hand geometry scanners are described in, for example, U.S. Pat. No. 5,483,601, entitled "Apparatus And Method For Biometric Identification Using Silhouette And Displacement Images Of A Portion Of A Person's Hand", U.S. Pat. No. 5,335,288, entitled "Apparatus And Method For Biometric Identification", both issued to Faulkner; U.S. Pat. No. 5,073,950, entitled "Finger Profile Identification System", issued to Colbert et al.; U.S. Pat. No. 5,073,949, entitled "Personal Verification Apparatus", issued to Takeda et al.; and U.S. Pat. No. 3,648,240, entitled "Personnel Identification Apparatus", issued to Jacoby et al.

Data collection station 11 also includes sample collection device or station 12 for collecting sample 14. In one preferred embodiment of data collection station 11, collection device 12 comprises a blood sample collection station. In another preferred embodiment, data collection station 12 comprises an oral mucosal transudate collection station. In yet another preferred embodiment, data collection station 12 comprises a urine sample collection stations.

Other types of samples (semen, hair, nail clippings, skin samples etc.) could be employed, however, at the present time, blood, urine or oral mucosal transudate samples are preferred for testing uniformity and accuracy. Urine specimen containers are available via Medline of Mundelein Ill. Blood specimen collection devices are available from a variety of sources including the Vacutainer line of sample collection devices available from Becton Dickenson Company (Rutherford N.J.). An oral mucosal transudate sample collection system specifically intended for HIV testing is marketed under the Orasure™ brand name by Epitope of Beaverton OR. Testing of hair samples is typically carried out using gas chromatography as is described, for example, in Detection of Antidepressant And Antipsychotic Drugs In Postmortem Human Scalp Hair", J. Couper et al., Journal of Forensic Sciences, JFSCA, Vol. 40, No. 1, January 1995, pp. 87–90, which is hereby incorporated herein by reference.

With all of these types of samples, it is established practice to label the sample container either prior to sample collection or after sample collection. The procedure described, for example, in The American Association Of Blood Banks Technical Manual, R. Walker, Ed.-in.-Ch., 11th Ed., 1993, pp. 14–17, on p. 15, specifies that all donor phlebotomy sample containers are to be labeled with donor identification at the donor chair but immediately prior to sample phlebotomy.

In many hospitals, it is written policy that the opposite occur, i.e., that phlebotomy occurs during which the test subject blood enters the test tube, which is only inscribed with indicia identifying the donor after sample donation. The potential for error is present in both procedures and especially in situations where several patients with similar names but differing blood characteristics are being evaluated under emergency conditions, i.e., following an automobile accident where a number of family members are all injured in a common vehicular disaster.

The procedure for hair sample collection is as follows: (i) client provides positive (e.g., photo) identification ("ID"); (ii) a copy of the client ID is stapled to requisition form; (iii) the client name etc. is filled out on the form, together with current date; (iv) the client reviews form for accuracy, (v) client signs release, (vi) the container label is prepared, including client name, test requested, date of collection and collector's initials, (vii) hair samples are taken from three different locations, preferably from the scalp but possibly also from armpit or chest; (viii) the collector initials seal, signs the requisition, records the date and time, lists any medications currently or recently taken and notes any abnormalities (baldness, short hair etc.) and puts the name of requesting organization (e.g., potential or present employer) on label. Upon receipt at the lab, only one sample is open at a time and the accessioner notes contents, date received and the like and provides the unopened container to the technician for testing.

When drug testing is linked to a database via a biodata key, it becomes possible for results to be registered or escrowed with a third party organization whereby a prospective employer may request a prospective employee to access his or her own prior drug test results. This arrangement does not result in liability to a prior employer of the prospective employee, because the prior employer does not provide the test data relevant to the prospective employee. Privacy is assured because the prospective employee (i) can only access results from his own drug tests and (ii) is free to choose not to provide the biometric scan required in order to access his or her own prior test data.

Additionally, it will be appreciated that sample collection station 12 may be employed, if desired, for conducting additional tests. For example, tests may be carried out for pubic lice, herpes, and/or antigens or antibodies associated with infectious diseases and any other infectious or communicable conditions of the test subject. This may include (i) those previously successfully treated but identifiable by remaining antibodies or other indicia in samples from the test subject, (ii) drugs used to treat sexually transmissible diseases and/or (iii) "recreational" drug use, especially that associated with risk of acquiring communicable diseases, for example, via sharing of hypodermic needles, as desired or required.

Sample collection station yields sample 14 and sample 14 is then (preferably simultaneously) labeled by labeling device 24. Labeling device 24 includes optional input port 26, whereby additional data may be entered (e.g., via a keyboard by medical personnel) for inclusion on the label of sample 14 and/or included with biometric correlation data and test date from biometric correlation device 18.

Labeling device 24 may be a laser printer, bar code printer or other printing or labeling device as is well known in the art. Biometric correlation data from biometric correlation device 18, a serial number or other correlating indicia, the date of the test and any other desired data are then linked together and supplied via external link 20 for shipment to database 39 (FIG. 3) via electronic link 20.

In a preferred embodiment of the instant invention, electronic link 20 is an encrypted digital link and may be effected via telephone line, for example. In a preferred embodiment of the instant invention, computer 13 supplies the serial number via link 15 to printer 19, which prints out slip 21 bearing the optional serial number for later use by the test subject.

The system of FIG. 2, wherein biometric scanner 18 is integrally combined with sample collection device 12 to provide combined scanner/sample collection device 12', is a preferred arrangement for the practice of the instant invention. By collecting sample 14 contemporaneously (and preferably simultaneously) with biometric indicia, assurance that sample 14 and the labeling biometric indicia correspond to one and the same person is provided without requiring the presence of a human monitor in order to ensure compliance. For example, a small blood sample is taken from the tip of one finger (e.g., the middle finger) during the scanning of biometric data from the test subject's hand or at least during a single insertion of the test subject's hand into combined scanner/sample collection device 12'.

This arrangement avoids a situation that could occur if the test subject were allowed to simply volunteer a previously-collected sample when having biometric data collected. In the latter scenario, there is no assurance that the sample actually came from the test subject, rather than the test subject's friend, child or pet. Apparatus for collection of small blood samples are well known in the medical industry where such procedures have been employed for decades for testing for, for example, phenylketonuria in newborns. Semi-automatic blood sample collection apparatus are well known in the industry.

Figure 3:
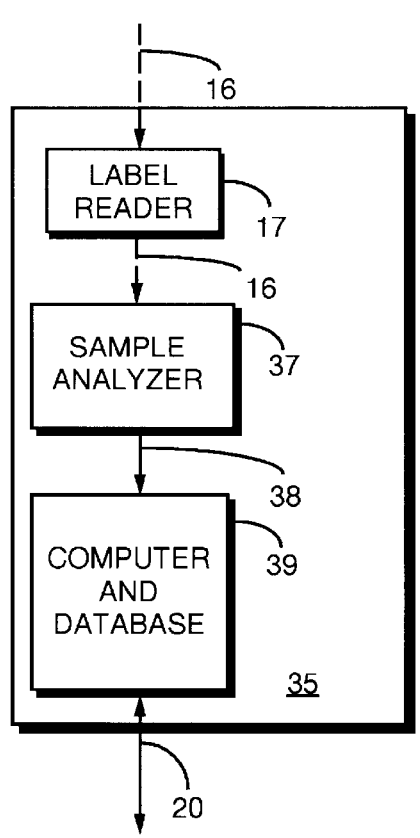
FIG. 3 is a schematic illustration of a biological sample analysis laboratory and computer data entry station of the instant invention.

Labeled sample 14 is transferred via link 16 to sample analysis station 35 of FIG. 3. Transfer via link 16 may be by common carrier to a remote site (e.g., a central testing facility) or to another room in the same facility. This could be effected via the Confide HIV Testing Service™ provided via Direct Access Diagnostics, a subsidiary of Johnson and Johnson, Inc. Direct Access Diagnostics has obtained FDA approval for an over-the-counter blood sample collection kit and testing procedure similar to the testing approach used by Planned Parenthood, i.e., providing the tested individual with great confidence in the accuracy of the test results but not providing a third party with any assurance that the test result corresponds to the presenting individual.

A first advantage of taking the test sample either under supervision of a neutral medical person or in conjunction with the collection of correlating biometric data is that this assurance can be provided to third parties. An additional advantage is realized in that the test subject needn't reveal a personal address or telephone number to an agency such as Direct Access Diagnostics, where this information might be discoverable by others. A further advantage accrues if the test subject can only activate access to the test results by first reviewing the test result with a trained counselor; in-person, face-to-face counseling with appropriate compassion and concern is then available to the test subject in the unfortunate event of a positive test result for HIV or other curable or incurable conditions. Other methods for providing link 16 and suitable testing facilities are available as well.

FIG. 3 is a schematic illustration of biological sample analysis laboratory and computer data entry/storage station 35 of the instant invention. Incoming samples 14 arrive via link 16 and are identified by label reader 17 to determine the serial number or other correlating indicia associated with the biometric data and to be associated with the results of analysis of sample 14. Sample 14 is supplied to sample analyzer 37 via link 16 and an analysis of the contents of sample 14 is performed and communicated to computer/database 39 via link 38. The results of the analysis of sample 14 are coupled to the biometric correlation data and, if desired, to the optional serial number by computer and database 39. At this point, the medical review officer (MRO) counsels A prior to the MRO filing A's data into database 39, and this counseling may be verified, if desired, by prompting eithr A ot the MRO, or each, and requesting confirmation via a fingerprint scan(s).

Figure 4:
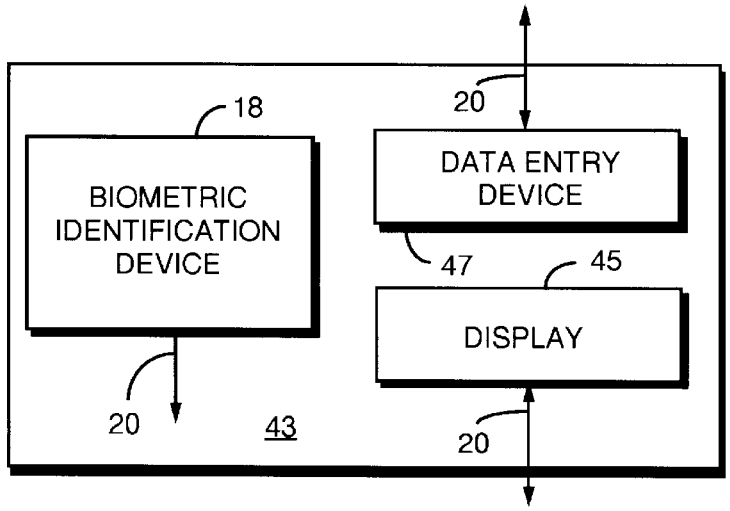
FIG. 4 is a schematic illustration of an embodiment of the data retrieval station of the instant invention.

FIG. 4 is a schematic illustration of an embodiment of data retrieval station 43 of the instant invention. Data retrieval station 43 includes biometric correlation device 18 coupled to database 39 of computer data entry station 35 (FIG. 3) via link 20. Data retrieval station 43 also includes display 45 and desirably includes data entry device 47. Data entry device 47 comprises a keyboard in a preferred embodiment of the instant invention. Data entry device 47 and display 45 are coupled to computer data entry station 35 (FIG. 3) and database 39 via link 20.

Figure 5:
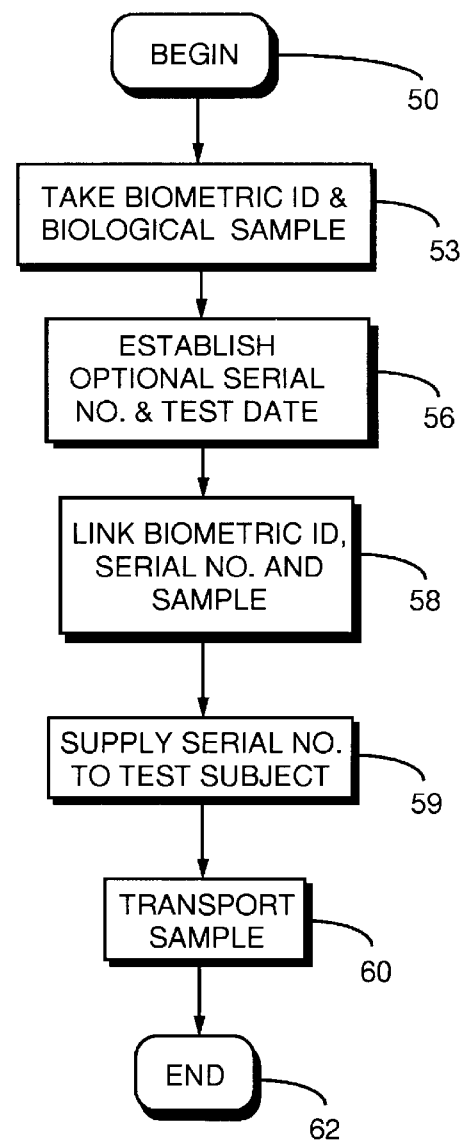
FIG. 5 is a flowchart describing steps involved in collecting (i) a biological sample from a test subject and (ii) simultaneously collecting correlating data pertinent to the test subject, in accordance with the teachings of the instant invention.

FIG. 5 is a flowchart describing steps involved in process 49 for collecting (i) biological sample 14 from a test subject and (ii) collecting correlating data pertinent to the test subject in accordance with the teachings of the instant invention. Process 49 begins (block 50) by taking a biometric correlation reading (block 52) which is digitized for further processing by computer/database 39 (FIG. 3) and which preferably is also linked to the date when the biometric data were taken.

A biological sample 14 is collected (block 54), preferably under the supervision of one or more witnesses to both sample collection and the taking of the biometric correlation reading (block 52) in order to ensure the integrity of the data collection and collation processes. The biological sample 14 may be a urine sample, a phlebotomy blood sample, an oral mucosal transudate sample, a breath sample, a hair or fingernail sample or other type of sample providing the medical or health data being determined.

Alternatively, sample collection (block 54) may be automated by, for example, combining a biometric scan with a urine sample collection device, blood sample collection device, an oral mucosal transudate collection device, a breath sample collection device, a hair or fingernail sample collection device or any other biological sample collection device such that sample 14 could only have come from the individual test subject from whom biometric correlation data were collected. When fluids representing biological samples are collected, additional confirmation of the integrity of the testing and correlation processes may be effected by determining the temperature of the collected sample (e.g., via a thermocouple, thermistor or liquid crystal thermometer) and/or by monitoring changes in electrical conductivity of the sample collection medium.

Similarly, a fingerstick blood sample collected simultaneously with a finger print biometric scan by drawing sample 14 from the finger from which the fingerprint is being taken and at the same time as the fingerprint is scanned provides similar assurances. These methods have the advantage of allowing the sample collection station to operate without requiring human operators while still protecting the integrity of the system, i.e., a third party could still reasonably have great confidence that the medical information derived from sample 14 corresponds to the individual providing matching biometric data.

A numeric correlation number or serial number is assigned (block 56) and this may be effected via either computer 13 within station 11 (FIGS. 1, 2) or by computer/database 39 of computer data entry station 35 (FIG. 3), with the latter being a preferred arrangement. The serial number, biometric data, test date and sample are linked (block 58) by (i) printing a correlating label on sample 14 container via labeling device 24 (FIGS. 1, 2) and (ii) transmission of the test date, biometric data and optional serial number via link 20 to computer/database 39 (FIG. 3). The serial number is desirably but optionally made available to the test subject (block 59) via slip 21 from printer 19 (FIGS. 1, 2). Labeled sample 14 is then transported (block 60) via link 16 (FIGS. 1, 2) to biological sample analysis laboratory and computer data entry station 35 (FIG. 3). The data collection process then ends (block 62).

Figure 6:
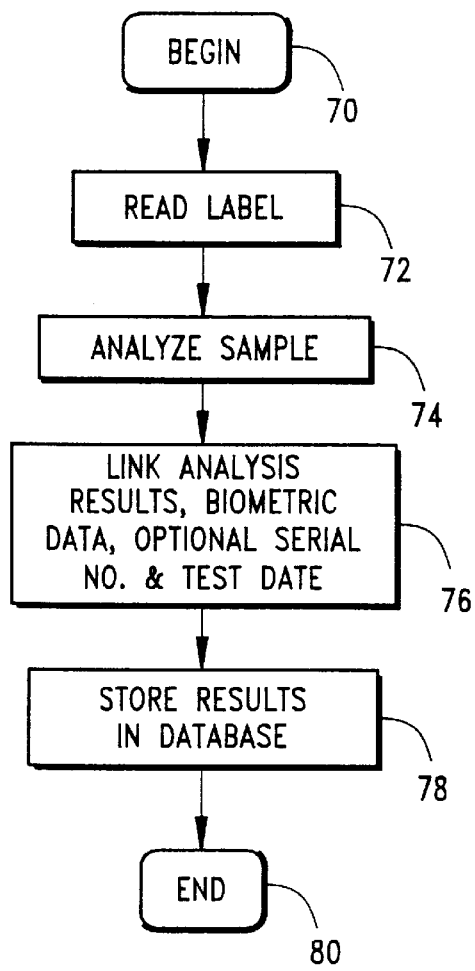
FIG. 6 is a flowchart describing steps involved in biological sample analysis laboratory and computer data entry, in accordance with the teachings of the instant invention.

FIG. 6 is a flowchart describing steps involved in biological sample analysis and computer data entry in biological sample analysis laboratory and computer data entry station 35 (FIG. 3) in accordance with the teachings of the instant invention. Process 69 begins (block 70) when incoming samples 14 are transported via link 16 to label reader 17 (FIG. 3) and the biodata, test date and/or optional serial number on the label of sample 14 are read (block 72) by label reader 17 (FIG. 3). Sample 14 is analyzed (block 74) to determine infectious status, presence of antigens or antibodies associated with past or present infectious disease of the test subject and/or presence of therapeutic or "recreational" drugs. The results of the analysis, preferably including the date when the analysis was performed and also preferably including data describing the test parameters and/or testing institution, are linked to the sample collection date, biometric correlation data and/or serial number (block 76) and are stored (block 78) in database 39 (FIG. 3). Analysis process 69 then ends (block 80).

Figure 7:
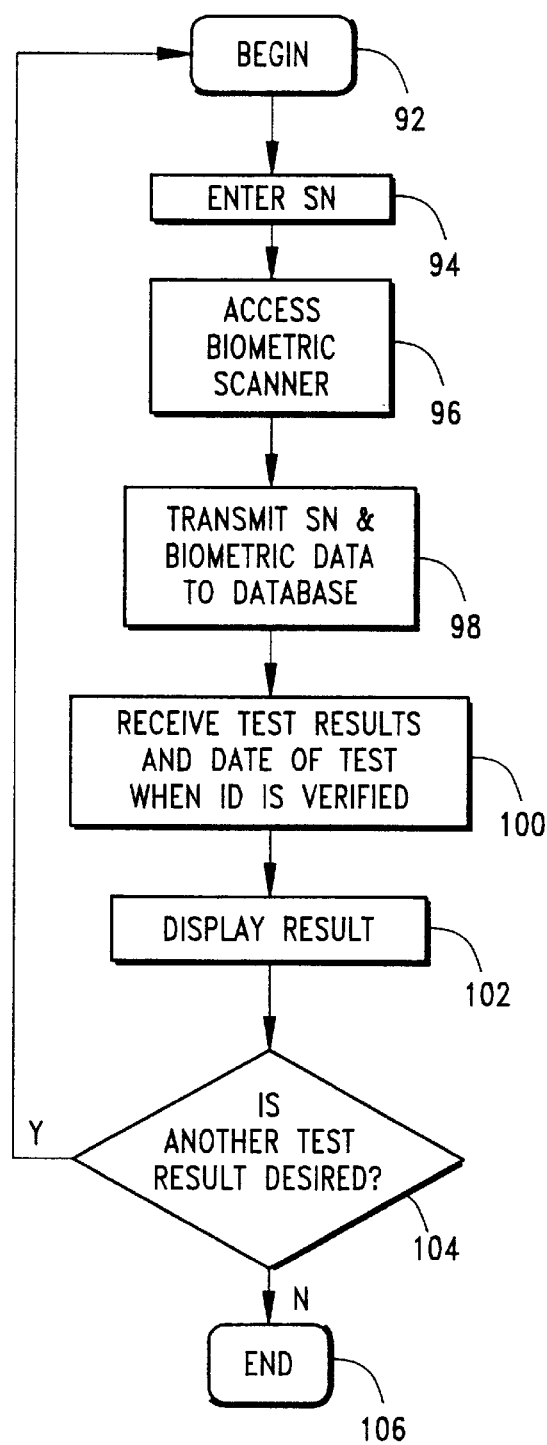
FIG. 7 is a flowchart describing steps involved in a first preferred embodiment of secure data retrieval, in accordance with the teachings of the instant invention.

FIG. 7 is a flowchart describing steps involved in a first secure data retrieval process 90 in accordance with the teachings of the instant invention. Data retrieval process 90 begins (block 92) with at least two parties (herein designated "A" and "B") who approach data retrieval station 43 (FIG. 4), although it will be appreciated that one party alone could retrieve medical data via such a system. "A" and "B" could, for example, be a couple who have recently met at a nightclub and who may have expressed mutual interest in sexual activity but who may also have concerns about the infectious status and/or drug treatment or use status of each other. "A" optionally enters a serial number SN (block 94) via data entry device 47 (FIG. 4) and also accesses (block 96) biometric correlation device 18 (FIG. 4).

Results are transmitted (block 98) to computer/database 39 (FIG. 3) via link 20. When a match is achieved between the optional serial number and the biometric correlation (collectively referred to as "ID") sent from data retrieval station 43 (FIG. 4) with those data stored in biological sample analysis laboratory and computer data entry station 35 (FIG. 3), the test results and date of the test are transmitted back via link 20 and are received (block 100) by data retrieval station 43 (FIG. 4). These results and the date of sample collection are then displayed (block 102) on display 45 (FIG. 4), where "A" and/or "B" may view them, after the system has provided to A advice that (i) a negative HIV test does not reflect events that have occurred after the test was administered and that (ii) safe sex is strongly recommended, even in the presence of a negative HIV test result. In one embodiment of the instant invention, A must verify that these caveats have been read and understood by providing an additional fingerprint scan to the system.

Data retrieval station 43, after a suitable interval or in response to signals from data entry device 47 (FIG. 4), then determines if a second set of data (corresponding to "B" in this example) are desired. When a second set of data are desired, process 90 loops back to entry of a second serial number (block 94) via data entry device 47 (FIG. 4) followed by "B's" accessing (block 96) biometric correlation device 18 (FIG. 4). Results corresponding to "B" are transmitted (block 98) to computer/database 39 (FIG. 3) via link 20, after the system has provided to B advice that (i) a negative HIV test does not reflect events that have occurred after the test was administered and that (ii) safe sex is strongly recommended, even in the presence of a negative HIV test result. In one embodiment of the instant invention, B must verify that these caveats have been read and understood by providing an additional fingerprint scan to the system.

When a match is achieved between the ID sent from data retrieval station 43 (FIG. 4) with those data stored in biological sample analysis laboratory and computer data entry station 35 (FIG. 3), the test results and date of sample collection are transmitted back via link 20 and are received (block 100) by data retrieval station 43 (FIG. 4). "B's" results and the date of the sample collection are then displayed (block 102) on display 45 (FIG. 4), where "A" and/or "B" may view them. When another set of data are not desired, the display is blanked (erased) and process 90 ends.

It will be appreciated that it is not to "A's" or "B's" advantage to present themselves in the above-described setting in order to learn the status of the test results for the first time. Additionally, it is desirable to provide counseling for persons who test positive, particularly for HIV, and for test results where there is a possibility of an indeterminate test result or of a false positive. Suitable compassion and counseling can be guaranteed if access to the system is only activated by mandatorily requiring the individual to present him- or her-self at a data retrieval station 43 where the individual and the counselor play roles analogous to those of "A" and "B", respectively, and review "A's" test results together in a private setting.

It will also be appreciated that in some settings, a single individual may wish to access their own data. For example, in the scenario where drug testing data are escrowed with a third-party agency, a prospective employer may invite a prospective employee to access the prospective employee's escrowed drug tests (and, desirably, dates of testing and analysis as well as test parameters, such as testing threshold levels employed to demarcate positive from negative test results, if applicable).

FIG. 8 is a flowchart describing user steps involved in a second preferred embodiment of a secure data retrieval system, in accordance with the teachings of the instant invention. In the second preferred embodiment of the instant invention, access is determined solely from biometric indicia. FIG. 8 shows steps taken by a user in process 190 to access previously-stored data, and begins (block 200) with the user dialing (block 202) a central computer facility (e.g., computer/database 39, FIG. 3), using the telephone keypad or using an automated dialing system. When more than one database is stored in the central computer, the user inputs a code or codes (block 204) to specify the particular database or databases desired to be accessed. The display or speaker provides confirmation (block 206) that the user has accessed the desired database.

The user then provides a biometric indicator (block 208), for example, by providing a fingerprint to a fingerprint scanning device, such as the SACMAN™ fingerprint analyzer. A signal, either audible or visible, is provided (block 210) to let the user know that the biometric data supplying step, e.g., fingerprint scan, was successful. The user then optionally presses a "TRANSMIT" button when the system is one that does not automatically send the biometric data. In either case, the biometric data are encrypted (block 212), if desired, and transmitted (block 214). The user's desired data are then made available (block 216), either as audible signals (e.g., synthesized speech) or as a computer display, when the biometric indicia match those of the party who donated the sample from which the data are derived. Process 190 then terminates (block 218). This process allows the user to access only data relevant to him or her self and provides assurance that other medical data are secure and can only be accessed by the person whom they describe.

FIG. 9 is a flowchart describing system steps involved in the second preferred embodiment of a secure data retrieval system, in accordance with the teachings of the instant invention. FIG. 9 illustrates steps in process 250 for providing data in response to biometric identification. In the central computer facility, the process begins (block 252) when a call is received (block 254). An acknowledgment signal is transmitted (block 256) to let the caller know that the system has been contacted. When the central computer facility includes more than one database, an access code must be supplied by the caller and received by the central computer facility (block 258) to specify the database or databases to be accessed.

When the central computer facility receives biometric data (block 260), these are decrypted (block 261), if necessary, and matched to stored biometric data (block 262). When the biometric data match stored biometric data, the associated records are transmitted back to the caller (block 264) and process 250 ends (block 270). When the biometric data do not match stored biometric data, the call is terminated (solid line, block 270) or a request for new or revised biometric data is sent to the caller (dashed line, block 266) and no stored information is released until the biometric data do match (blocks 260–262). The call then terminates (block 270).

It will be appreciated that stored data may have come from another source, i.e., from a testing system outside of the system described thus far. In these instances, when it is determined that the data provide an acceptable degree of integrity, these are linked to biometric data from the test subject, preferably along with data describing the provenance of the test data (including test dates, sample collection dates and the like), and the resultant composite record is stored in a fashion analogous to that used for data derived from test samples taken as indicated hereinabove.

It will also be appreciated that in some settings, a doctor may wish to be able to store medical information in such a fashion that it can only be recalled by the patient. For example, with genetic testing for various disorders and abnormalities, there may be concern that these data, if made available or seized from the doctor, could be used to discriminate against the individual. Some fear that if the genetic test results were known to industry, discrimination may occur against individuals with genetic predisposition to disease. Governmental and private concern for implications of a positive genetic test result, as for example for BRCA1, are well known. For further example, President Clinton indicated recently that a law would be proposed that makes it illegal for an insurance company to restrict coverage where a person has a genetic test result indicating possible future disease is likely.

The need for individuals to know their own genetic predisposition and medical personnel to watch for and screen for any such disease development is key. Despite potential governmental regulations which offer protection from discrimination based on genetic predisposition, a means for allowing medical care while keeping test results private is seen. The invention herein disclosed is one method and system that can accomplish this by only allowing the test results to be viewed when the patient to whom the results are pertinent provides a biometric identification.

§ III. EXAMPLES

Several examples of devices and systems for collecting a variety of biological samples from a test subject and labeling the sample container with information relating the sample to the test subject are illustrated in FIGS. 10–15. These systems describe specific embodiments adapted to be labeled, for example, with data corresponding to fingerprint data (e.g., data such as that generated in the SACMAN system; these data are not necessarily fingerprint images but do correspond to data taken from fingerprints and therefore correlate positively with the individual providing the fingerprint data).

A. Urine collection device.

Figure 10:
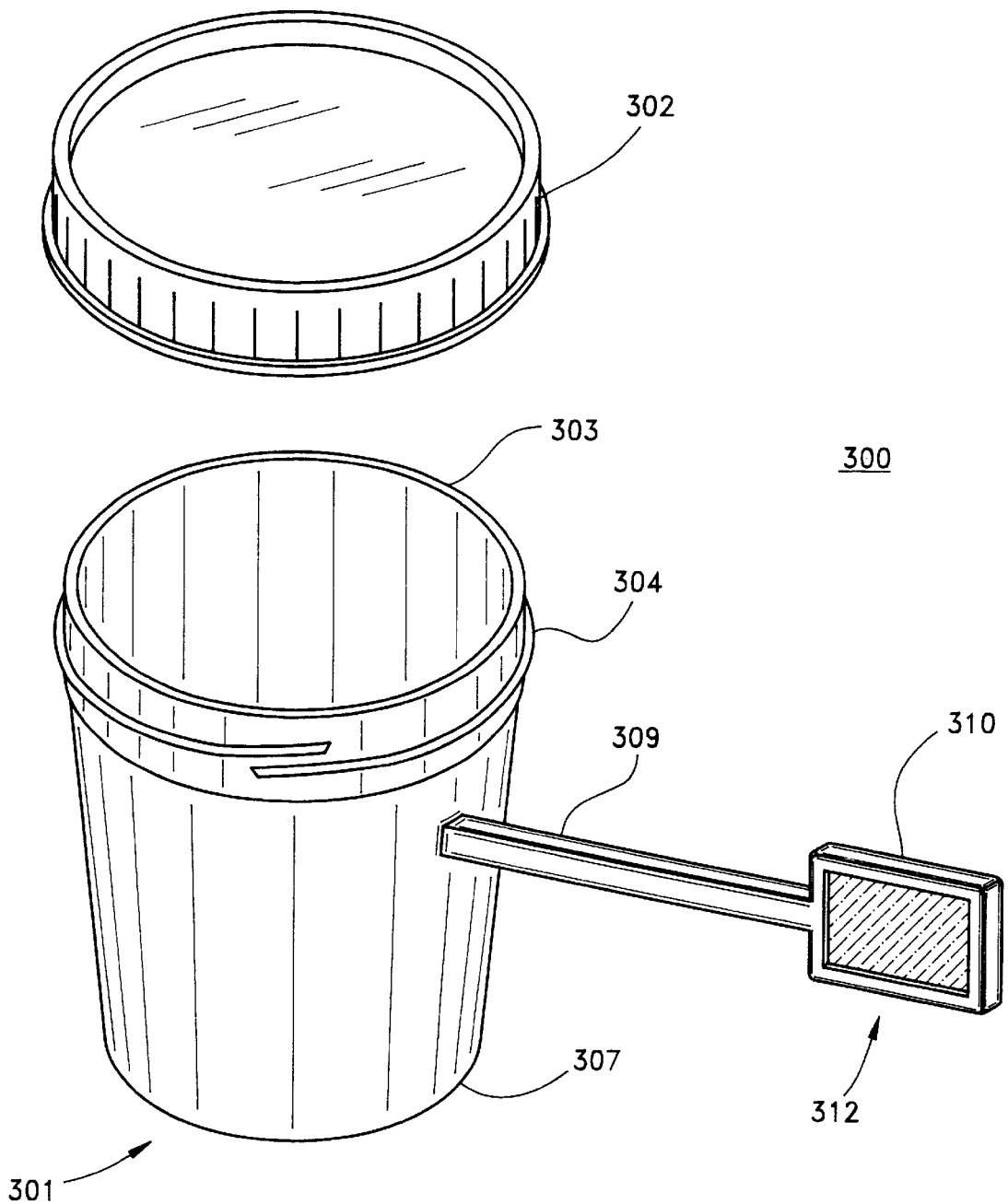
FIG. 10 illustrates a first preferred embodiment of a urine specimen container adapted to accept data corresponding to a urine donor, in accordance with the teachings of the instant invention.

FIG. 10 illustrates a first preferred embodiment of a urine specimen container system 300 adapted to accept data corresponding to a urine donor, in accordance with the teachings of the instant invention. The urine specimen container system 300 comprises a cap or lid 302 and a body 301. The body 301 includes a cup 307 adapted to hold urine and includes means 304 adapted to secure the lid 302 to the body 301/cup 307, such as threads, disposed at an open end 303 of the cup 307.

Also coupled to the specimen collection cup 307 is an attachment apparatus such as a bar or stick 309 having a first end attached to the cup 307 and a second end bearing a recording medium 312. In the embodiment illustrated, the recording medium is an area 310 adapted to be inserted into a printer 322 (see FIG. 11). Other types of recording media, such as a memory chip, may also be usefully employed together with an appropriate instrument for writing data thereto. It is also desirable to include a date of sample collection in the data that are transferred to the recording medium.

FIG. 10 illustrates a first embodiment of a urine collection device 300 allowing simultaneous collection of urine and biometric data and further allowing data derived from the biometric data to be affixed to a nominally flat surface or tag 312 coupled to the urine collection device 301. In one embodiment, a printer 322 (FIG. 11) is affixed to a toilet 320 and positioned to allow printing on the tag 312 while the urine collection device 301 is collecting the urine specimen. By placing the tag 312 into the printing slot on the printer 322, the urine collection cup or reservoir 301 is confined to the area of the toilet 320. When the tag 312 is secured to the reservoir 301 by an angulated, rigid rod or shaft 309, the reservoir 301 is placed over the toilet bowl 320 in the vicinity of the toilet bowl opening into which urination normally occurs. The rod or shaft 309 is long enough so that the urination process typically does not result in urine being splashed or sprayed onto the printer 322, the biometric data collection device 324 or the computer.

In the course of donating a sample, the urine donor 328 obtains a urine container 300 and removes the threaded top 302. The tag 309 is inserted into the printer slot. The donor 328 then places the right forefinger 329 on the scan surface of a fingerprint scanning device 324 such as the SAC-MAN™ fingerprint scanner. The scanner 324 scans the fingerprint and, when it is determined that a viable fingerprint has been scanned, signals the donor 328, for example via a visible or audible indicator. The donor 328 then urinates into the reservoir 301 while the printer 322 is recording the biometric data or information derived from the biometric data on the tag 312. The donor 328 then replaces the reservoir top 302 and removes the tag 309 from the printer 322.

It will be appreciated that the tag 309 may be coupled via a flexible interconnection, such as a string or chain, to accommodate persons who need to position the reservoir 301 in order to be able to urinate into the reservoir 301, and that other types of recording media may be usefully employed for storage of the biometric information. For example, a chip could be built into the urine collection reservoir 301, which chip is coupled to a small antenna built into the wall of the reservoir 301. The antenna allows for power to be electromagnetically coupled to the chip when it is in the vicinity of another antenna (e.g., built into or mounted on the toilet bowl 320) that is supplying the electrical power. These antennae also permit data to be written to the chip and read from the chip, much as data are read in electronic toll collection devices deployed around the nation. Alternatively, a physical electrical interconnection could be employed, much as data are read from and written to "smart cards" used for financial transactions.

Figure 11:
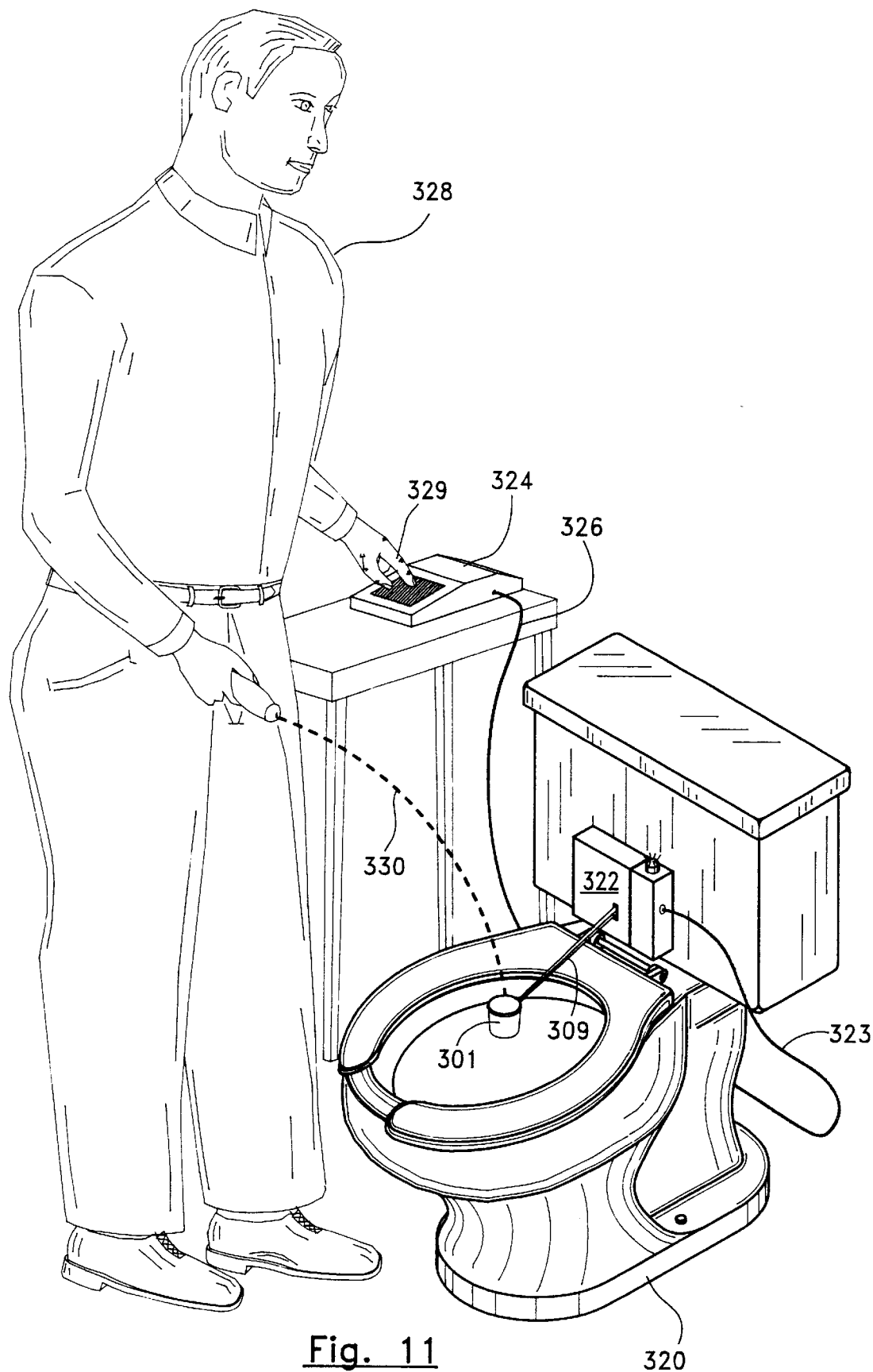
FIG. 11 illustrates usage of a urine and data collection system, in accordance with the teachings of the instant invention.

FIG. 11 illustrates usage of a preferred embodiment of the urine and data collection system 300 of FIG. 10, in accordance with the teachings of the instant invention. A user 328 prepares to urinate into a toilet 320 equipped with a printer 322 for coupling to the body 301 of the urine specimen container system 300. When, for example, the forefinger 329 of the left hand of the user 328 is scanned by the scanner 324, data corresponding to a fingerprint of the user 328 are sent via interconnection 326 and these data or data derived therefrom or linked thereto are sent to the printer 322 via link 323 and are printed by the printer 322 on the surface 310 of the tab 312 that is coupled to the body 307 of the urine collection cup system 301. Desirably, collection of the urine stream 330 is temporally coincident with collection and writing of fingerprint data to the specimen collection cup 301.

This method has the advantage that the data identifying the specimen are not encoded onto the lid 302 of the urine specimen container system 300. This method provides a further advantage in that it prevents incorrect association of one test subject'ample with another test subject'urine by inadvertent switching of lids 302 between two different specimen sample containers.

It will be appreciated that detectors may be included in the scanner 324 to assess finger temperature and that sensors included with the urine specimen container system 300 can be employed to verify (i) the temperature of the specimen, (ii) that the specimen is being provided while the fingerprint is being scanned, or that the delay between initiation of these two events is only one, two, three, four or five seconds or an appropriate interval and/or (iii) that the conductivity of the specimen is appropriate for human urine.

B. Phlebotomy collection system.

Figure 12:
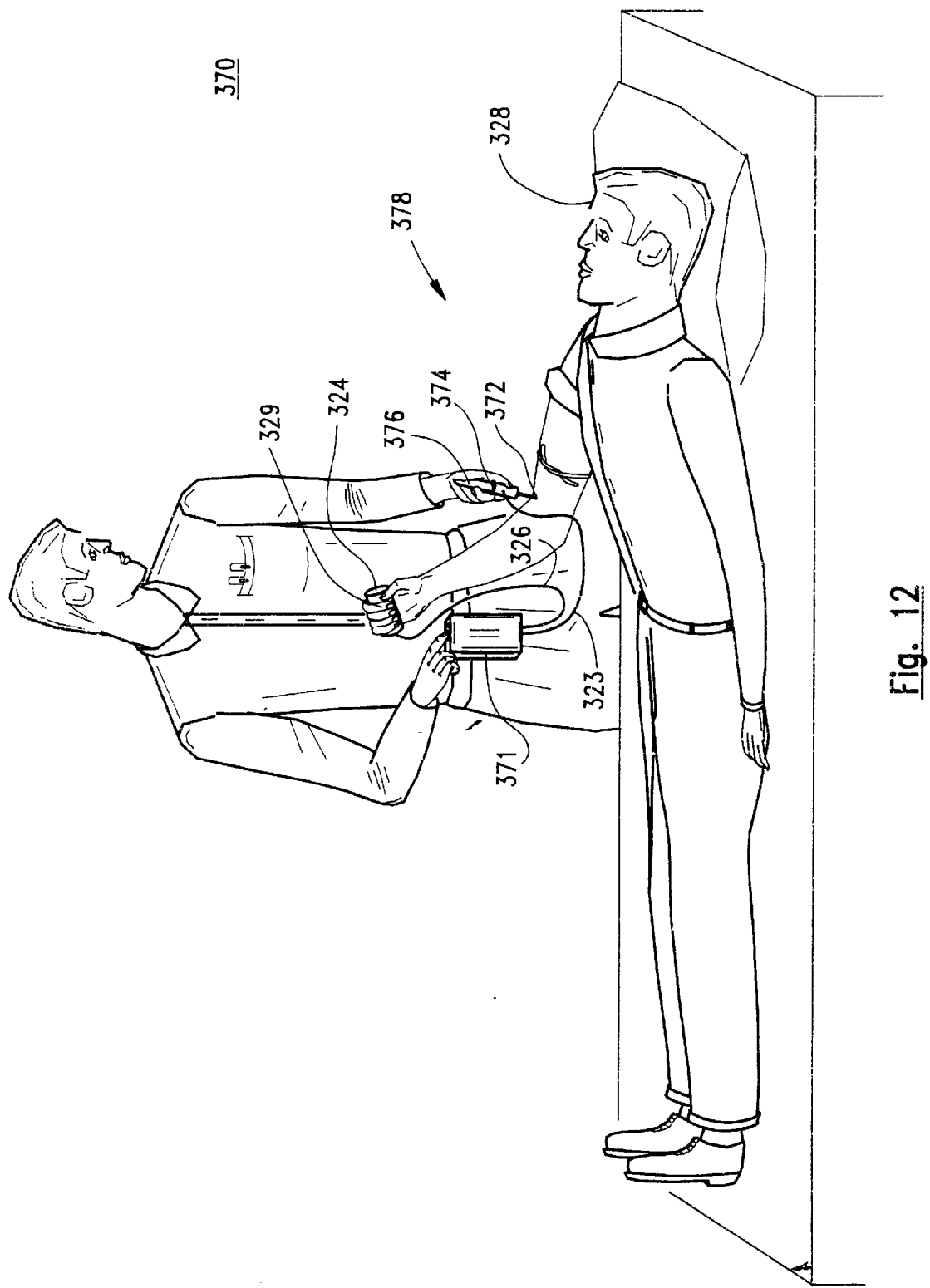
FIG. 12 illustrates a phlebotomy and data collection system, in accordance with the teachings of the instant invention.

FIG. 12 illustrates an embodiment of a phlebotomy and data collection system 370, in accordance with the teachings of the instant invention. The phlebotomy and data collection system 370, in a preferred embodiment, includes a processor 371 having a first link 323 coupled to a device 374 for encoding or transferring data corresponding to the test subject on or in a specimen collection device such as a blood collection tube. The specimen collection device 378 includes, for example, a curved surface adapted to receive printed indicia from a printer (analogous to printer 322 of FIGS. 11 and 12), or a memory chip or other read/write data storage and retrieval apparatus. The specimen collection device 378 also includes a needle 372 adapted for collection of a blood sample from the user 328.

In this phlebotomy and data collection system 370, the biometric data may be a fingerprint taken from, for example, the right forefinger 329 of the test subject 328. This can be effected by including a fingerprint scanning device (analogous to fingerprint scanner 324 of FIGS. 11 and 12) in the grip that is used by the test subject to compress to facilitate blood flow into the vein used for phlebotomy and data collection system 370.

It will be appreciated that other data may be collected by sensors built into the grip as well. For example, temperature and grip strength may be measured to verify that a human is gripping the grip (or, more accurately, to determine when a human is NOT gripping the grip). Again, by encoding or transferring the data to the specimen container itself, the possibility for mislabeling or for inadvertently switching labels between containers is eliminated, providing a high degree of confidence in the integrity of the provenance of these data. It is also desirable to include a date of sample collection in the data that are transferred to the recording medium associated with the sample container.

C. Oral mucosal transudate collection system.

In a preferred embodiment, the instant invention contemplates an oral mucosal transudate collection device that is also adapted to (i) meet the ergonomic constraints imposed by the human body and (ii) record biometric indicia, or data corresponding thereto, for later pairing of the results of medical tests on the oral mucosal transudate with the donor of the oral mucosal transudate. The device comprises a shaft, preferably angulated, fashioned of any suitable material such as plastic having a pad disposed at a first end for collection of oral mucosal transudate and including a surface disposed at a second end for recording of dermatoglyphics of the donor's fingerprints or data corresponding thereto.

The oral mucosal transudate desired for this collection device comprise saliva and oral mucosal transudate. Oral mucosal transudate is derived from blood and includes antibodies indicative, for example, of prior infection. In the Orasure device manufactured by Epitope of Beaverton OR, this is effected by osmotically drawing blood materials including antibodies from the blood vessels of the cheek and oral cavity via hypertonic saline materials included in the pad.

Pads suitable for use in collecting immunoglobins and other materials from the oral cavity are described in U.S. Pat. Nos. 5,103,836 ("Oral Collection Device And Ket For Immunoassay") and 5,335,673 ("Oral Collection Device And Method For Immunoassay"), both issued to Goldstein et al. and apparatus for the immunoassay is described in U.S. Pat. No. 5,234,001 ("Container For Immunoassay With Frangible Nipple"), which patents are hereby incorporated herein for their teachings relative to oral sample collection.

Preferred pad materials include thick, absorbent cotton paper such as product #300 manufactured by Schleicher and Schuell in Keene NH. Preferably, the pad is treated with a hypertonic solution (e.g., NaCl) such that the concentration of salt in the pad exceeds that found in blood. Desirably, a non-specific binding agent and a preservative are also included in the pad material, as described by Goldstein et al. Pads of this type may be used to test for a variety of disease antibodies and may also be employed to determine presence of a variety of drugs in body fluids.

In a first preferred embodiment, the dermatoglyphic data recording medium comprises a surface adapted to permit printing of data corresponding to dermatoglyphic data, preferably disposed at an end of the oral mucosal transudate collection device remote from the end employed for collection of the oral mucosal transudate. Alternatively, the dermatoglyphic data recording medium may comprise a memory device embedded within the oral mucosal transudate collection device and accessed via either a radio link or a physical interconnection.

In use, the test subject places the oral mucosal transudate collection device in the mouth such that the pad for collection of oral mucosal transudate is appropriately disposed within the oral cavity for the recommended period of time. This task occupies one hand, leaving the fingers of the other hand free for collection of dermatoglyphic data corresponding to the test subject. These data or data derived therefrom are recorded on the dermatoglyphic data recording medium, either simultaneously with data and sample collection or contemporaneously therewith.

In a second preferred embodiment, the dermatoglyphic recording pad comprises a waxy surface for recording fingerprints, which surface is covered with a protective layer prior to use. The protective layer is removed to allow recording of the fingerprint information as the donor picks the device up to place the pad into the donor's mouth.

After the sample is secured, the dermatoglyphic information from the donor that is recorded on the instrument may be visually compared to a line vector printout of a fingerprint from data stored in memory in a SACMAN™ system. The dermatoglyphic data are broken down into indicia that allow reliable and repeatable correlation with stored dermatoglyphic data at a later time.

In either of these embodiments, linking the results of tests done on the oral mucosal transudate on the pad to the dermatoglyphic data from the fingerprint analysis tool, the same donor may retrieve the data from the tests by providing the dermatoglyphic data, as discussed infra in conjunction with FIGS. 8 and 9 and associated text.

There is a natural anatomical angle at which the human hand holding an object between the straight forefinger and straight thumb approaches the mouth of the individual holding the object. This angle is mirrored for the left hand versus the right, meaning that either turning the angled shaft over or providing a wishbone-shaped structure allows accommodation of either right- or left-handed test subjects without compromise of the ergonomic benefits of the bent shaft on the sample collection device.

The right hand holding a flat object between the straight forefinger and straight thumb approaches the mouth in a natural manner in which the forefinger is more or less horizontal and the thumb crosses the fingerprint area of the forefinger at an angle of approximately 45 degrees. The natural holding grasp of the right hand as the hand approaches the mouth is such that the forefinger and thumb compress each other in a manner wherein the lateral aspect of the forefinger and the medial aspect of the thumb meet. The oral secretion collection device usefully includes a fingerprint imprint area at an angle such the forefinger fingerprint pad aspect of the forefinger meets, over a wide area, the surface of the fingerprint imprint aspect of the collection device, and the thumb meets a brace allowing the test subject to comfortably hold the device in a natural manner while applying pressure from the thumb to the forefinger and thus applying the fingerprint of the forefinger to the biometric identification surface of the sample collection device.

It will be appreciated that the forefinger aspect of the holding area in the second preferred embodiment has a substance suitable to accept and preserve the forefinger fingerprint for later comparison by visual inspection to data taken by the fingerprint reading device. This material is typically a waxy or adhesive substance or the like that is covered prior to use by a layer of, for example, cellophane or plastic sheeting. The cover is removed immediately prior to use, thus allowing the forefinger dermatoglyphic pattern of fingerprint arches, swirls and whorls typically used to identify the individual based on the fingerprint of the user test subject when the test subject grasps the holding area of the sample collection device.

The natural angle for placing a device held between the distal phalanxes of the straight right forefinger and the straight right thumb against the inside of the right cheek is approximated by bringing the tip of the straight right forefinger to the right corner of the mouth while the distal phalanx of the right forefinger is pressed to the distal phalanx of the straight right thumb. This angle is approximately 120 degrees as measured from the line of the straight forefinger to the line of occlusion of the right upper and lower molars. This natural angle is disclosed as the optimal angle between the holding aspect of the sample collection device and the plane of the pad for the oral mucosal transudate collection aspect of the device.

Figure 13:
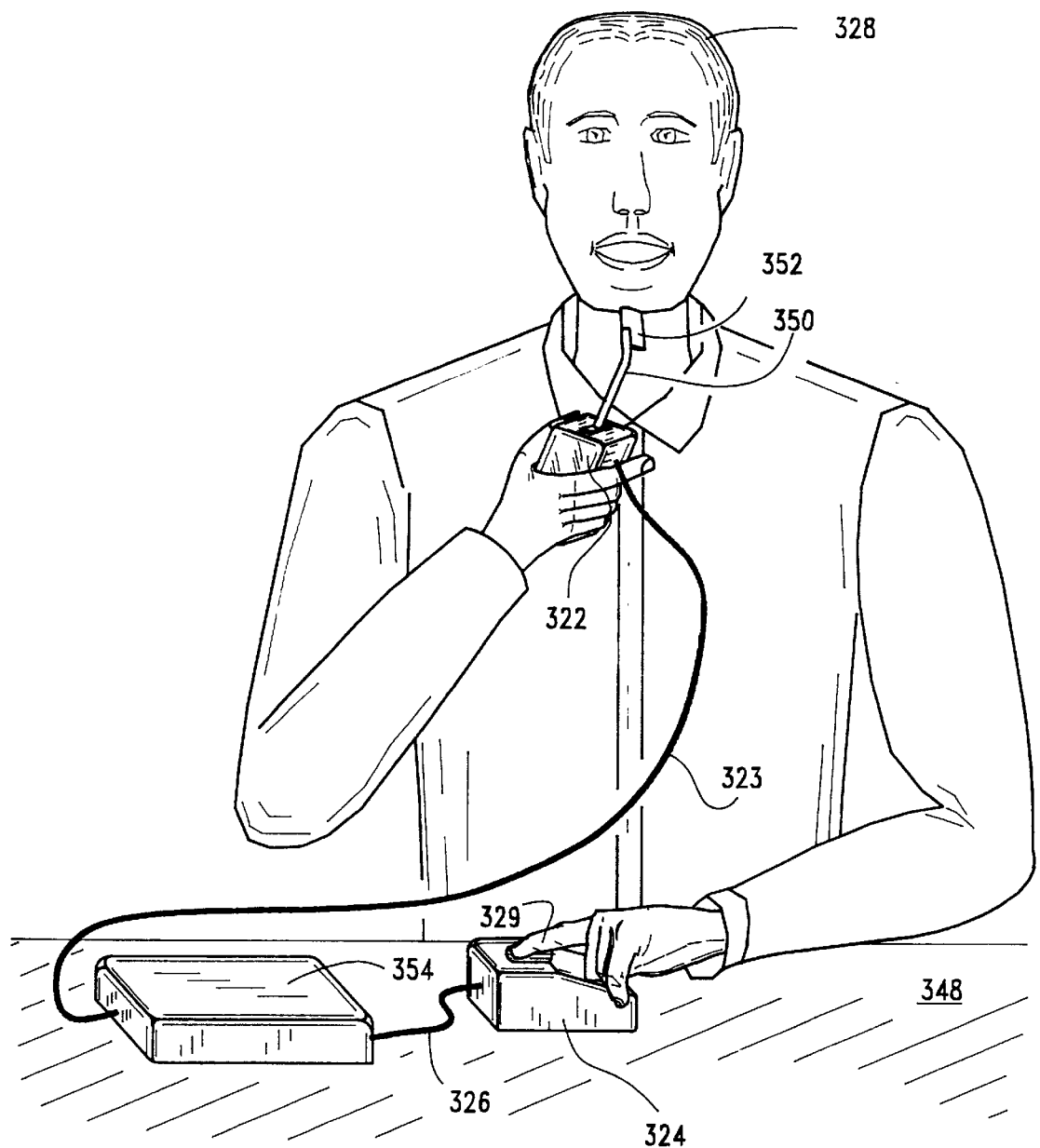
FIG. 13 illustrates usage of an oral mucosal transudate and data collection system, in accordance with the teachings of the instant invention.

FIG. 13 illustrates usage of an embodiment of an oral mucosal transudate and data collection system 348, in accordance with the teachings of the instant invention. In this embodiment, a first end of an oral sample collection device 350 is adapted to receive data, in much the manner described above with respect to urine specimen collection system 300. A second end 352 is prepared to accept a sample from the oral cavity of the user 328. A biometric scanner such as a fingerprint scanning device 324 is coupled via link 326 to a computer 354, which is in turn coupled via link 323 to a device 322 for encoding or otherwise transferring data corresponding to the collected biometric data. In this example, the biometric data are taken from the user's left forefinger 329.

Again, it will be appreciated that sensors within the oral mucosal transudate collection pad 352 may be employed to determine that the (i) pH, salinity etc. are appropriate for human oral mucosal transudate, (ii) temperature of the oral mucosal transudate collection pad 352 is appropriate to a human oral cavity and (iii) that the oral mucosal transudate are collected at the same time as the biometric data.

D. Breathalyzer data collection.

Figure 14B:
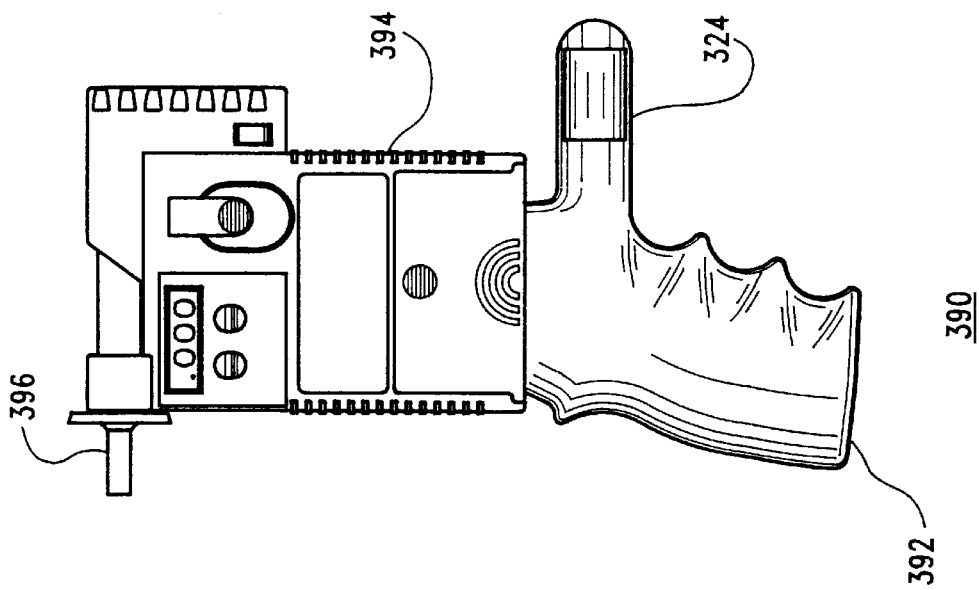
FIGS. 14A and 14B illustrate a breathalyzer and data collection system, in accordance with the teachings of the instant invention.
Figure 14A:
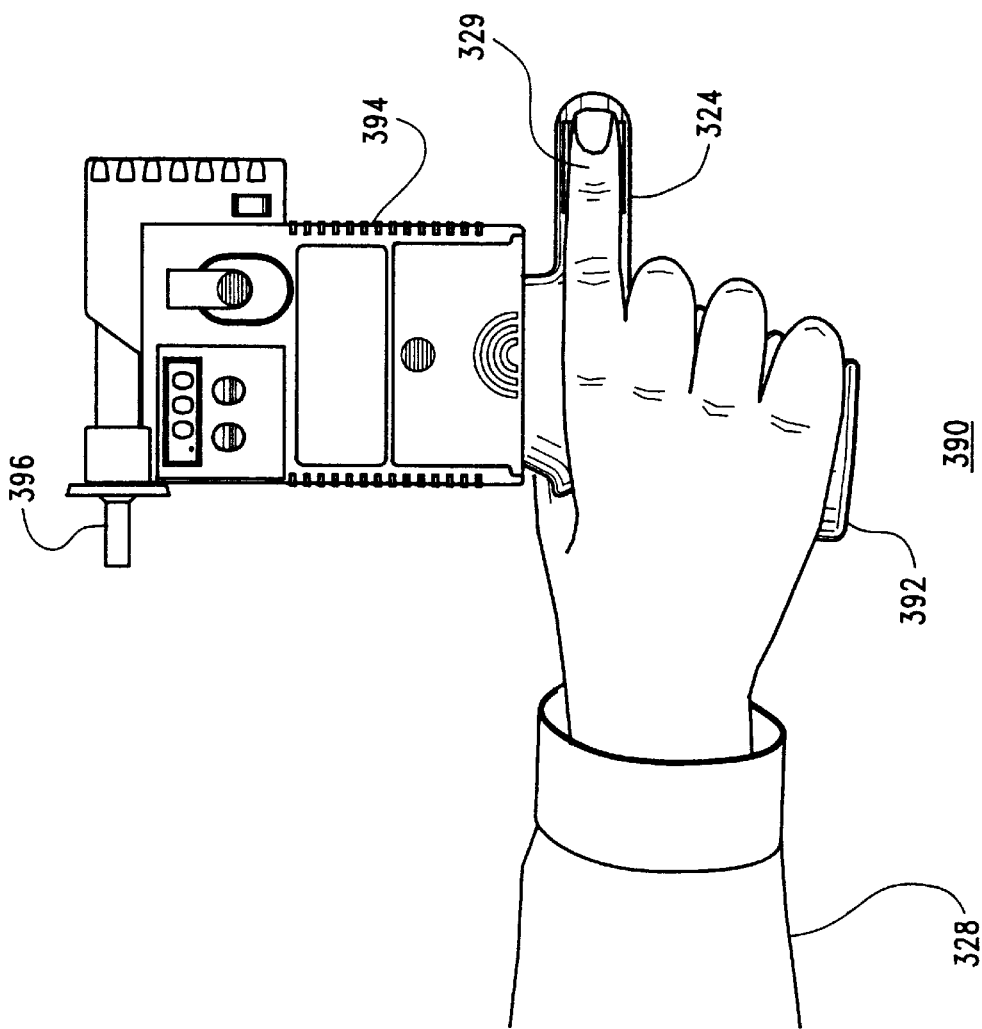

FIGS. 14A and 14B illustrate a breathalyzer and data collection system 390, in accordance with the teachings of the instant invention. The breathalyzer system 390 includes a fingerprint scanning device 324 adapted, for example, to scan the right forefinger fingerprint of the test subject when the test subject (i) grips the gripping handle 392 and (ii) provides a breath sample via port 396. In this embodiment, any processing of the fingerprint or other biometric data occurs in a processor that is integral to the breathalyzer 394, which also analyzes breath products and provides, for example, breath alcohol or alcohol metabolite data. These two test results are linked and stored within a memory contained in the body 394 of the breathalyzer device. Other data that are desirably linked to and stored with the fingerprint data and the results of the analysis of breath products include the date and time when the breath sample was collected.

E. Hair sample collection.

Figure 15:
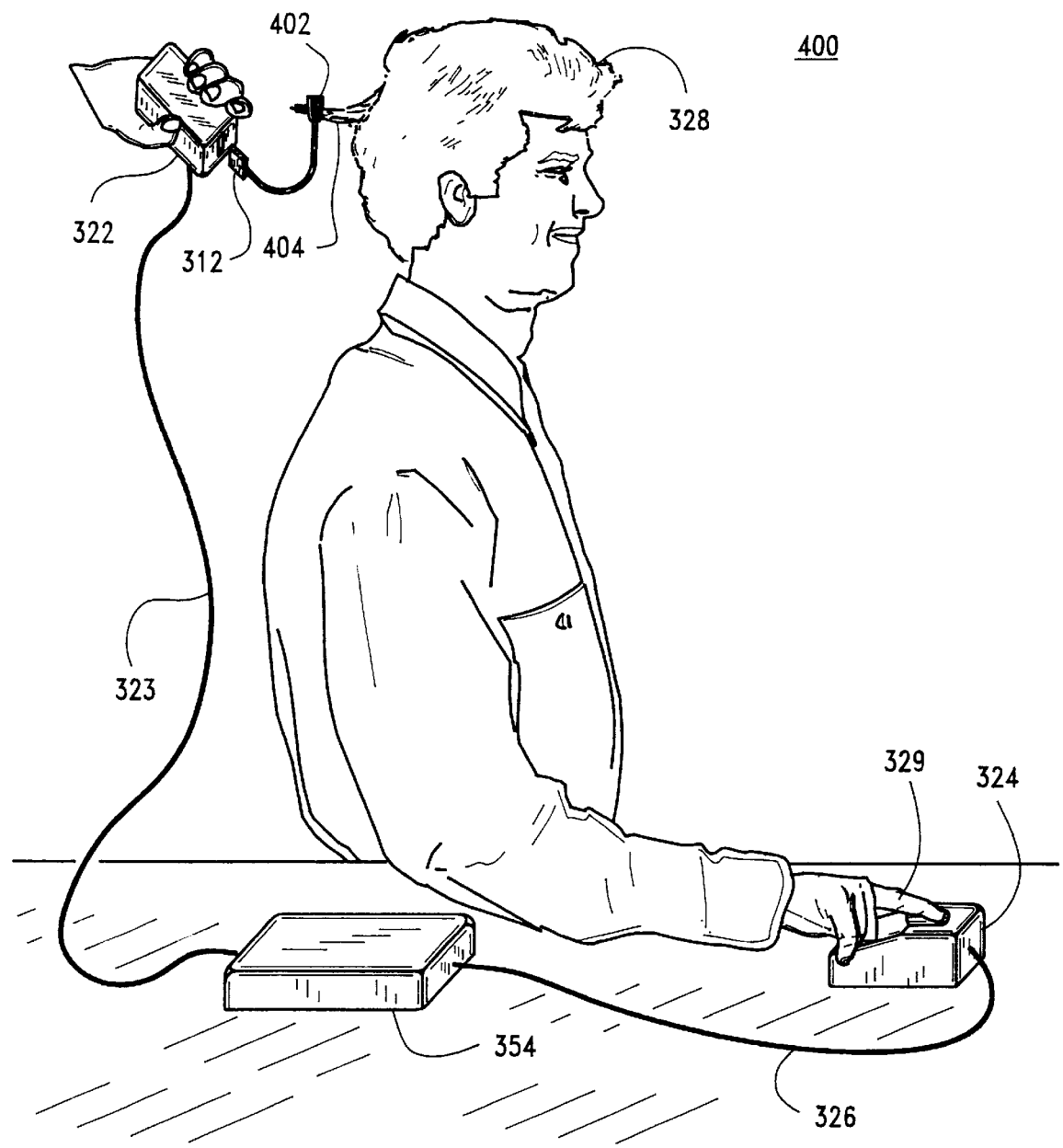
FIG. 15 illustrates a hair sample and data collection system, in accordance with the teachings of the instant invention.

FIG. 15 illustrates an embodiment of a hair sample and data collection system 400, in accordance with the teachings of the instant invention. In this system, a barrette-like device 402 is used to clamp a portion of the test subject's hair 404.

The barrette-like device 402 comprises a clam-shell type of arrangement and includes apparatus for (i) determining when the clam-shell type of device is closed, (ii) determining that biometric indicia have been collected, (iii) recording data corresponding to the biometric indicia (and also preferably the sample collection date) and (iv) preventing further opening and closing of the clam-shell device by the test subject once the biometric data (and preferably also the date of sample collection) are transferred thereto. Alternatively, verification that the collection device 402 is closed may be by visual inspection by medical personnel.

Fingerprint data are taken via fingerprint reader 324 from the forefinger 329 of the sample donor 328. Information corresponding to the fingerprint data are sent to computer 354 via interconnection 326 and then to the printer 322 via interconnection 323. The printer 322 prints data corresponding to the fingerprint information on the tag 312. Alternatives for storing the fingerprint or other biometric data in association with the sample are possible as discussed above with respect to the other examples.

The foregoing detailed description of the instant invention for the purposes of explanation have been particularly directed toward separate facilities for data storage and data retrieval. It will be appreciated that the invention is equally useful for systems where data storage is also performed at each data retrieval station, for example.

It will be appreciated that a system for (optionally, anonymously) testing for infectious disease and/or associated antigens or antibodies and/or other therapeutic or "recreational" drugs has been described that does not require the test subject to carry any identification card or to provide any photograph or home address to the system has been described. The system permits twenty-four hour access to the data in a fashion that (i) provides high credibility to the user as to the accuracy of the test result and the applicability of the test result to the user and (ii) provides high credibility to another person that the test results and test sample collection date correspond to the observable user and accurately reflect the infectious/communicable status of the test subject and/or presence of associated antigens or antibodies and/or other therapeutic or "recreational" drugs as of the date of sample collection, without compromise of the identity of the user or of the identity of the another person.

It will be appreciated that need for a serial number or at least need for the test subject to have any knowledge of a serial number could be eliminated by employing the biometric data alone as means for accessing the system. Measurement of finger temperature or observation of the scanning process by both parties each provide assurance that no facsimile of a fingerprint is being employed to "fool the system".

However, use of a serial number does require that the parties employing data retrieval station 43 (FIG. 4) both be conscious and also requires voluntary compliance with the data retrieval process. Use of "stress codes" (i.e., codes which inactivate the opening of a closed area and also silently notify authorities) in security systems is widespread and similar procedures may be incorporated into the system of the instant invention in order to obviate abuse of the system or of users of the system. Accordingly, use of a serial number in data retrieval is desirable in some kinds of situations.

Various changes and modifications to the embodiment herein chosen for purposes of illustration will readily occur to those skilled in the art. For example, other types of diseases or genetic predispositions may be tested for, to effectuate a combination of capabilities as may be desired for a specific application. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. An apparatus for collecting medical specimens from a voluntary test subject, said apparatus comprising:

a sample collection apparatus for collecting a biological sample from said test subject; and a biometric data storage device, said biometric data storage device coupled to said sample collection apparatus, said biometric data storage device for storing biometric data electronically permitting positive correlation of test results from said biological sample biometrically with said test subject.

2. The apparatus of claim 1, further comprising an apparatus for labeling a biological sample container with said biometric data, said biometric data collected temporally coincident with said biological sample.

3. The apparatus of claim 2, wherein apparatus for labeling said biological sample container includes a printer adapted to print indicia corresponding to said biometric data.

4. The apparatus of claim 1, wherein said sample collection apparatus includes an apparatus chosen from a group consisting of: a urine sample collection device, a blood sample collection device, an oral mucosal transudate collection device, a fingernail sample collection device and a hair sample collection device.

5. The apparatus of claim 1, wherein said sample collection apparatus comprises an oral pad treated with hypertonic saline solution, said oral pad for collecting oral mucosal transudate.

6. The apparatus of claim 5, further comprising an apparatus for labeling a biological sample container with data corresponding to said biometric data.

7. The apparatus of claim 6, wherein said apparatus for labeling said biological sample container includes a printer adapted to print indicia corresponding to said biometric data.

8. The apparatus of claim 1, wherein said biometric data collection device includes a fingerprint scanning device and said sample collection apparatus and said fingerprint scanning device comprise a single unit adapted to collect said biometric data temporally coincident to said biological sample collection.

9. The apparatus of claim 1, wherein said sample collection apparatus comprises a cup adapted to accept urine.

10. The apparatus of claim 9, wherein said biometric data storage device includes a fingerprint scanning device.

11. The apparatus of claim 10, wherein said biometric data storage device includes a printer adapted to print indicia corresponding to said biometric data.

12. An apparatus for collecting medical specimens from a voluntary test subject, said apparatus comprising:

a sample collection apparatus comprising an oral pad treated with hypertonic saline solution, said oral pad for collecting oral mucosal transudate from said test subject;

a biometric data storage device, said biometric data storage device coupled to said sample collection apparatus, said biometric data storage device for storing biometric data collected temporally coincident with said oral mucosal transudate and permitting positive correlation of said oral mucosal transudate with said test subject.

13. The apparatus of claim 12, wherein said biometric data storage device comprises an area on said sample collection apparatus suitable for printing of biometric data.

14. The apparatus of claim 12, wherein said biometric data storage device comprises an area disposed on a distal end of a handle coupled to said oral pad, said area permitting data derived from fingerprint scanning to be written thereto via a printer.

15. An apparatus for collecting medical specimens from a voluntary test subject, said apparatus comprising:

a urine collection cup for collecting a urine sample from said test subject; and a biometric data storage device, said biometric data storage device coupled to said urine collection cup, said biometric data storage device for storing biometric data collected temporally coincident with said urine sample and permitting positive correlation of said urine sample with said test subject.

16. The apparatus of claim 15, wherein said biometric data storage device includes a fingerprint scanning device.

17. The apparatus of claim 16, wherein said biometric data storage device includes a printer adapted to print indicia corresponding to said biometric data.

* * * * *